United States Patent [19]

Wehner et al.

[11] Patent Number: 6,005,117
[45] Date of Patent: Dec. 21, 1999

[54] IMINO COMPOUNDS, PROCESS FOR THEIR PREPARATION AND THEIR USE AS VICTRONECTIN ANTAGONISTS

[75] Inventors: Volkmar Wehner, Sandberg; Jochen Knolle, Kriftel; Hans Ulrich Stilz, Frankfurt, all of Germany; Jean-Francois Gourvest, Claye Souilly; Denis Carniato, Clamart, both of France; Thomas Richard Gadek, Oakland, Calif.; Robert McDowell, San Francisco, Calif.; Robert Maurice Pitti, El Cerrito, Calif.; Sarah Catherine Bodary, San Bruno, Calif.

[73] Assignee: Hoechst Aktiengesellschaft, Frankfurt, Germany

[21] Appl. No.: 08/899,887

[22] Filed: Jul. 24, 1997

[30] Foreign Application Priority Data

Jul. 24, 1996 [DE] Germany .............. 196 29 817

[51] Int. Cl.⁶ ............ C07D 233/44; C07D 233/66; A61K 31/415
[52] U.S. Cl. ............ 548/332.5; 514/398; 548/326.5
[58] Field of Search .............. 548/332.5; 514/398

[56] References Cited

U.S. PATENT DOCUMENTS

| | | | |
|---|---|---|---|
| 3,516,995 | 6/1970 | Houlihan et al. | 548/332.5 |
| 3,528,968 | 9/1970 | Houlihan et al. | 548/332.5 X |
| 3,931,152 | 1/1976 | Tomcufcik et al. | 548/332.5 X |
| 4,152,436 | 5/1979 | Drabb | 424/251 |
| 4,322,422 | 3/1982 | Addor et al. | 424/251 |
| 5,543,433 | 8/1996 | Doetzer et al. | 514/638 |

FOREIGN PATENT DOCUMENTS

| | | |
|---|---|---|
| 0 518 586 | 6/1992 | European Pat. Off. |
| 0 528 586 | 8/1992 | European Pat. Off. |
| 0 528 587 | 8/1992 | European Pat. Off. |
| WO 95/32710 | 5/1993 | WIPO |
| WO 94/08577 | 10/1993 | WIPO |
| WO 94/12181 | 11/1993 | WIPO |
| WO 96/00574 | 6/1995 | WIPO |
| WO 96/00730 | 6/1995 | WIPO |

OTHER PUBLICATIONS

Friedlander, et al., "Definition of Two Angiogenic Pathways by Distance $\alpha_v$ Integins", Science 270:1500–02 (Dec. 1995).

Brown, et al., "Stimulation of migration of human aortic smooth muscle cells by vitronectin: implications for atherosclerosis", Cardiovascular Research 1994; 28:1815–1820.

Fisher, et al. "Inhibition of osteoclastic bone resorption in vivo by echistatin, an 'arginyl–glycyl–aspartyl' (RDG)–containing protein", Endocrinology vol. 132:3 1411–13, (1993).

Sato, et al. "Echistatis is a potent inhibitor of bone resorption in culture" J. Cell Bio. 111, Oct. 1990 1713–1723.

Horton, et al. "Arg–Gly–Asp (RGD) peptides and Anti–Vitronectin Receptor Antibody", Experimental Cell Research 195, 368–375 (1991).

Brooks, et al. "Integrin$\alpha_v\beta_3$ antagonists promote tumor regression by inducing apoptosis", Cell, vol. 79, 1157–1164 (Dec. 1994).

*Primary Examiner*—Floyd D. Higel
*Attorney, Agent, or Firm*—Foley & Lardner

[57] ABSTRACT

There are described imino derivatives of formula (I)

$$R^1-Y-A-B-D-E-F-G \qquad (I)$$

their preparation and their use as medicaments. The compounds according to the invention may be used as vitronectin receptor antagonists and as inhibitors of bone resorption.

17 Claims, No Drawings

IMINO COMPOUNDS, PROCESS FOR THEIR PREPARATION AND THEIR USE AS VICTRONECTIN ANTAGONISTS

BACKGROUND OF THE INVENTION

1. Field of the Invention

The present invention relates to compounds of the formula I and their physiologically tolerable salts and pharmaceutical preparations comprising such compounds, their preparation and use as medicaments, in particular as inhibitors of bone resorption by osteoclasts, as inhibitors of tumor growth and tumor metastasis, as antiinflammatories, for the treatment or prophylaxis of cardiovascular disorders such as arteriosclerosis or restenosis, for the treatment or prophylaxis of nephropathies and retinopathies, such as, for example, diabetic retinopathy, and as vitronectin receptor antagonists for the treatment and prophylaxis of illnesses which are based on the interaction between vitronectin receptors and their ligands in cell—cell or cell-matrix interaction processes. The invention furthermore relates to the use of the compounds of the formula I and their physiologically tolerable salts and pharmaceutical preparations comprising those compounds as medicaments for the alleviation or cure of illnesses which are caused at least partially by an undesired extent of bone resorption, angiogenesis, or proliferation of cells of the vascular smooth musculature.

2. Description of Related Art

Human bones undergo a continuous dynamic renovation process which involves bone resorption and bone formation. These processes are controlled by types of cell specialized for this. Bone formation is based on the deposition of bone matrix by osteoclasts, bone resorption is based on the degradation of bone matrix by osteoclasts. The majority of bone disorders are based on a disturbed equilibrium between bone formation and bone resorption. Osteoporosis is characterized by a loss of bone matrix. Activated osteoclasts are polynuclear cells having a diameter of up to 400 μm, which remove bone matrix. Activated osteoclasts accumulate on the surface of the bone matrix and secrete proteolytic enzymes and acids into the so-called "sealing zone", the region between their cell membrane and the bone matrix. The acid environment and the proteases bring about the degradation of the bone.

Studies have shown that the accumulation of osteoclasts on the bone is controlled by integrin receptors on the cell surface of osteoclasts.

Integrins are a superfamily of receptors which include, inter alia, the fibrinogen receptor $\alpha_{IIb}\beta_3$ on the blood platelets and the vitronectin receptor $\alpha_v\beta_3$. The vitronectin receptor $\alpha_v\beta_3$ is a membrane glycoprotein which is expressed on the cell surface of a number of cells such as endothelial cells, cells of the vascular smooth musculature, osteoclasts and tumor cells. The vitronectin receptor $\alpha_v\beta_3$ which is expressed on the osteoclast membrane controls the process of accumulation on the bone and bone resorption and thus contributes to osteoporosis.

$\alpha_v\beta_3$ in this case binds to bone matrix proteins such as osteopontin, bone sialoprotein and thrombospontin, which contain the tripeptide motif Arg-Gly-Asp (or RGD).

Horton and co-workers describe RGD peptides and an anti-vitronectin receptor antibody (23C6), which inhibit tooth destruction by osteoclasts and the migration of osteoclasts (Horton et al., Exp. Cell. Res. 1991, 195, 368). In J. Cell Biol. 1990, 111, 1713, Sato et al. describe echistatin, an RGD peptide from snake venom, as a potent inhibitor of bone resorption in a tissue culture and as an inhibitor of osteoclast attachment to the bone. Fischer et al. (Endocrinology, 1993, 132, 1411) were able to show in the rat that echistatin also inhibits bone resorption in vivo.

The vitronectin receptor $\alpha_v\beta_3$ on human cells of the vascular smooth musculature of the aorta stimulates the migration of these cells into the neointima, which finally leads to arteriosclerosis and restenosis after angioplasty (Brown et al., Cardiovascular Res. 1994, 28, 1815).

Brooks et al. (Cell 1994, 79, 1157) show that antibodies against $\alpha_v\beta_3$ or $\alpha_v\beta_3$ antagonists can bring about a shrinkage of tumors by inducing the apoptosis of blood vessel cells during angiogenesis. Chersh et al. (Science 1995, 270, 1500) describe anti-$\alpha_v\beta_3$ antibodies or $\alpha_v\beta_3$ antagonists which inhibit bFGF-induced angiogenesis processes in the rat eye, which could be useful therapeutically in the treatment of retinopathies.

The Patent Application WO 94/12181 describes substituted aromatic or nonaromatic ring systems and WO 94/08577 describes substituted heterocycles as fibrinogen receptor antagonists and inhibitors of platelet aggregation. EP-A-518 586 and EP-A-528 587 disclose aminoalkyl- or heterocyclyl-substituted phenylalanine derivatives, and WO 95/32710 discloses aryl derivatives as inhibitors of bone resorption by osteoclasts. WO 96/00574 describes benzodiazepines, and WO 96/00730 describes fibrinogen receptor antagonist templates, in particular benzodiazepines which are linked to a nitrogen-bearing 5-membered ring, as vitronectin receptor antagonists.

SUMMARY OF THE INVENTION

One object of the present invention is to provide compounds and their pharmacologically tolerable salts capable of being used as inhibitors of bone resorption by osteoclast, as inhibitors of tumor growth and tumor metastasis, as antiinflammatories, for the treatment or prophylaxis of cardiovascular disorders such as arteriosclerosis or restenosis, for the treatment or prophylaxis of nephropathies and retinopathies and as vitronectin receptor antagonists for the treatment and prophylaxis of illnesses which are based on the interaction between vitronectin receptors and their ligands in cell—cell or cell-matrix interaction processes. Another object of the invention is to provide compounds which can be used as carriers for active compounds in order to transfer the active compounds specifically to the site of action.

Another object of the invention is to provide a pharmaceutical preparation which includes the compound of the present invention. Still another object of the invention is to provide methods for the production of compounds of the present invention. Still another object of the present invention is to provide methods for the treatment of the conditions described above.

In accomplishing the foregoing objects, there has been provided according to one aspect of the present invention, compounds of the formula I

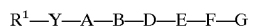

in which:

A is a direct bond, $(C_1-C_8)$-alkanediyl, $-NR^2-N=CR^2-$, $-NR^2-C(O)-NR^2-$, $-NR^2-C(O)O-$, $NR^2-C(O)S-$, $-NR^2-C(S)-NR^2-$, $-NR^2-C(S)-O-$, $-NR^2-C(S)-S-$, $-NR^2-S(O)_n-NR^2-$, $-NR^2-S(O)_n-O-$, $-NR^2-S(O)$ $_n$—, $(C_3-C_{12})$-cycloalkanediyl, —C≡C—, —NR$^2$—C(O)—, —C(O)—NR$^2$—, —$(C_5-C_{14})$-arylene-C(O)—NR$^2$, —O—, —S(O)$_n$—, —$(C_5-C_{14})$-arylene-, —CO—, —$(C_5-C_{14})$-arylene-CO—, —NR$^2$—, —SO$_2$—NR$^2$—, —CO$_2$—, —N═CR$^2$—, —R$^2$C═N—, —CR$^2$═CR$^3$—, —$(C_5-C_{24})$-arylene-S(O)$_n$—, which can in each case be mono- or disubstituted by $(C_1-C_8)$-alkanediyl, such as, for example, —$(C_1-C_8)$-alkanediyl-CO—NR$^2$—$(C_1-C_8)$-alkanediyl, —$(C_1-C_8)$-alkanediyl-CO—NR$^2$— or —CO—NR$^2$—$(C_1-C_8)$-alkanediyl;

B is a direct bond, $(C_1-C_8)$-alkanediyl, —CR$^2$═CR$^3$— or —C≡C—, which in each case can be mono- or polysubstituted by $(C_1-C_8)$-alkanediyl, such as, for example, —CH$_2$—C≡C—CH$_2$—, —CH$_2$—CR$^2$═CR$^3$—, or a divalent radical of a 5- or 6-membered saturated or unsaturated ring, which can contain 1 or 2 nitrogen atoms and can be mono- or disubstituted by $(C_1-C_6)$-alkyl or doubly bonded oxygen or sulfur;

D is a direct bond, $(C_1-C_8)$-alkanediyl or —O—, —NR$^2$—, —CO—NR$^2$—, —NR$^2$—CO—, —NR$^2$—C(O)—NR$^2$—, —NR$^2$—C(S)—NR$^2$—, —OC(O)—, —(CO)O—, —CO—, —CS—, —S(O)—, —S(O)$_2$—, —S(O)$_2$—NR$^2$—, —NR$^2$—S(O)—, —NR$^2$—S(O)$_2$—, —S—, —CR$^2$═CR$^3$—, —C≡C—, —NR$^2$N═CR$^2$—, —N═CR$^2$—, —R$^2$C═N— or —CH(OH)—, which in each case can be mono- or disubstituted by $(C_1-C_8)$-alkanediyl;

E is a 6-membered aromatic ring system, which optionally contains up to 4 nitrogen atoms and is optionally substituted by 1–4 identical or different radicals from the group consisting of R$^2$, R$^3$, fluorine, Cl, Br, I, NO$_2$ and OH;

F is defined as D;

G is

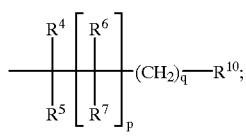

Y is a direct bond or —NR$^2$—;

R$^1$ is R$^2$—C(═NR$^2$)—NR$^2$—, R$^2$R$^3$N—C(═NR$^2$)—, R$^2$R$^3$N—C(═NR$^2$)—NR$^2$—, or a 4–10-membered mono- or polycyclic aromatic or nonaromatic ring system, which can optionally contain 1–4 heteroatoms from the group consisting of N, O and S and can optionally be monosubstituted or polysubstituted by substituents from the group consisting of R$^{12}$, R$^{13}$, R$^{14}$ and R$^{15}$;

R$^2$, R$^3$ independently of one another are H, $(C_1-C_{10})$-alkyl which is optionally mono- or polysubstituted by fluorine, $(C_3-C_{12})$-cycloalkyl, $(C_3-Cl_2)$-cycloalkyl-$(C_1-C_8)$-alkanediyl, $(C_5-C_{14})$-aryl, $(C_5-C_{14})$-aryl-$(C_1-C_8)$-alkanediyl, H$_2$N, (R$^8$O)R$^8$NR$^9$, R$^8$OR$^9$, R$^8$OC(O)R$^9$, R$^8$-$(C_5-C_{14})$-arylene-R$^9$, R$^8$R$^8$NR$^9$, HO—$(C_1-C_8)$-alkanediyl—NR$^8$R$^9$, R$^8$R$^8$NC(O)R$^9$, R$^8$C(O)NR$^8$R$^9$, R$^8$C(O)R$^9$, R$^8$R$^8$N—C(═NR$^8$)—, R$^8$R$^8$N—C(═NR$^8$)—NR$^8$— or $(C_1-C_{18})$-alkylcarbonyloxy-$(C_1-C_6)$-alkanediyloxycarbonyl;

R$^4$, R$^5$, R$^6$, R$^7$ independently of one another are H, fluorine, OH, $(C_1-C_8)$-alkyl, $(C_3-C_{12})$-cycloalkyl, $(C_3-C_{12})$-cycloalkyl-$(C_1-C_8)$-alkanediyl, or R$^8$OR$^9$, R$^8$SR$^9$, R$^8$CO$_2$R$^9$, R$^8$OC(O)R$^9$, R$^8$—$(C_5-C_{14})$-arylene-R$^9$, R$^8$N(R$^2$)R$^9$, R$^8$R$^8$NR$^9$, R$^8$N(R$^2$)C(O)OR$^9$, R$^8$S(O)$_n$N(R$^2$)R$^9$, R$^8$OC(O)N(R$^2$)R$^9$, R$^8$C(O)N(R$^2$)R$^9$, R$^8$N(R$^2$)C(O)N(R$^2$)R$^9$, R$^8$N(R$^2$)S(O)$_n$N(R$^2$)R$^9$, R$^8$S(O)$_n$R$^9$, R$^8$SC(O)N(R$^2$)R$^9$, R$^8$C(O)R$^9$, R$^8$N(R$^2$)C(O)R$^9$, R$^8$N(R$^2$)S(O)$_n$R$^9$;

R$^8$ is H, $(C_1-C_8)$-alkyl, $(C_3-C_{12})$-cycloalkyl, $(C_3-C_{12})$-cycloalkyl-$(C_1-C_8)$-alkanediyl, $(C_5-C_{14})$-aryl, $(C_5-C_{14})$-aryl-$(C_1-C_8)$-alkanediyl, it being possible for the alkyl radicals to be mono- or polysubstituted by fluorine:

R$^9$ is a direct bond or $(C_1-C_8)$-alkanediyl;

R$^{10}$ is C(O)R$^{11}$, C(S)R$^{11}$, S(O)$_n$R$^{11}$, P(O)(R$^{11}$)$_n$ or a four- to eight-membered, saturated or unsaturated heterocycle which contains 1, 2, 3 or 4 heteroatoms from the group N, O, S, such as, for example, tetrazolyl, imidazolyl, pyrazolyl, oxazolyl, thiadiazolyl;

R$^{11}$ is OH, $(C_1-C_8)$-alkoxy, $(C_5-C_{14})$-aryl-$(C_1-C_8)$-alkanediyloxy, $(C_5-C_{14})$aryloxy, $(C_1-C_8)$-alkylcarbonyloxy-$(C_1-C_4)$-alkanediyloxy, $(C_5-C_{14})$-aryl-$(C_1-C_8$-alkanediylcarbonyloxy-$(C_1-C_6)$-alkanediyloxy, NH$_2$, mono- or di-$(C_1-C_8$-alkyl)-amino, $(C_5-C_{14})$-aryl-$(C_1-C_8)$-alkanediylamino, $(C_1-C_8)$-dialkylaminocarbonylmethylenoxy, $(C_5-C_{14})$-aryl-$(C_1-C_8)$-dialkylaminocarbonylmethylenoxy or $(C_5-C_{14})$-arylamino or a radical of an L- or D-amino acid;

R$^{12}$, R$^{13}$, R$^{14}$, R$^{15}$ independently of one another are H, $(C_1-C_{10})$-alkyl, which is optionally mono- or polysubstituted by fluorine, $(C_3-C_{12})$-cycloalkyl, $(C_3-C_{12})$-cycloalkyl-$(C_1-C_8)$-alkanediyl, $(C_5-C_{14})$-aryl, $(C_5-C_{14})$-aryl-$(C_1-C_8)$-alkanediyl, H$_2$N, (R$^8$O)R$^8$NR$^9$, R$^8$OR$^9$, R$^8$OC(O)R$^9$, R$^8$R$^8$NR$^9$, R$^8$—$(C_5-C_{14})$-arylene-R$^9$, HO—$(C_1-C_8)$-alkanediyl-N(R$^2$)R$^9$, R$^8$N(R$^2$)C(O)R$^9$, R$^8$C(O) N(R$^2$)R$^9$, R$^8$C(O)R$^9$, R$^2$R$^3$N—C(═NR$^2$)—NR$^2$—, R$^2$R$^3$N—C(═NR$^2$)—, ═O, ═S;

n is 1 or 2;

p, q independently of one another are 0 or 1;

in all their stereoisomeric forms and mixtures thereof in any ratio; and their physiologically tolerable salts, where in the compounds of the formula I at least one of the groups A, D or F is —NR$^2$—N═CR$^2$—, —N═CR$^2$— or —R$^2$C═N—.

According to another aspect of the invention, there has been provided a pharmaceutical composition which includes a compound of the formula I and at least one pharmaceutically innocuous excipient and/or additive.

According to another aspect of the present invention, there has been provided a process for the preparation of a compound of the formula I in which R$^1$—Y—A— is

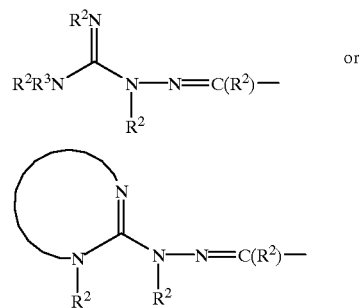

and B, D, E, F, G, R$^2$ and R$^3$ are defined as above, which comprises carrying out a fragment condensation of compounds of the formula

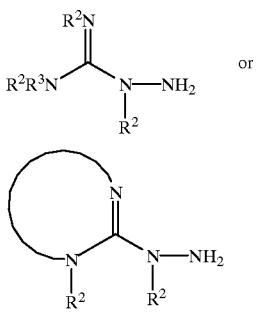

with ketones or aldehydes preferably of the type O=C(R²)—, in which R² and R³ are as defined above, or corresponding acetals or ketals.

According to still another aspect of the present invention, there has been provided a process for the preparation of a compound of the formula I in which F is —C(O)NR²— and R¹, Y, A, B, D, E and G are defined as above which comprises carrying out a fragment condensation of a compound of the formula II

with HR²N—G, where R¹, R², Y, A, B, D, E and G are defined as above and M is hydroxycarbonyl, $(C_1-C_6)$-alkoxycarbonyl, or activated carboxylic acid derivatives.

According to still another aspect of the present invention, there has been provided a method for inhibiting bone resorption by osteoclasts, inhibiting tumor growth and tumor metastasis, reducing inflammation, treating or preventing cardiovascular disorders, for treating or preventing nephropathies and retinopathies or for the treatment and prevention of diseases which are based on the interaction between vitronectin receptors and their ligands in cell—cell or cell-matrix interaction processes, comprising administering a therapeutically effective amount of the compound of the formula I and/or of a physiologically tolerable salt thereof to an human or animal in need thereof.

Further objects, features and advantages of the present invention will become apparent from the detailed description of preferred embodiments which follows.

DETAILED DESCRIPTION OF PREFERRED EMBODIMENTS

The alkyl radicals occurring in the substituents of the compound of formula I can be straight-chain or branched, saturated or mono- or polyunsaturated. The same applies to radicals derived therefrom, such as, for example, alkoxy. Cycloalkyl radicals can be mono- , bi- or tricyclic.

Monocyclic cycloalkyl radicals can include, in particular, cyclopropyl, cyclobutyl, cyclopentyl, cyclohexyl, cycloheptyl and cyclooctyl, which, however, can also be substituted by, for example, $(C_1-C_4)$-alkyl. Examples of substituted cycloalkyl radicals which may be mentioned are 4-methylcyclohexyl and 2,3-dimethylcyclopentyl.

Bicyclic and tricyclic cycloalkyl radicals can be unsubstituted or substituted in any desired suitable positions by one or more oxo groups and/or one or more identical or different $(C_1-C_4)$-alkyl groups, e.g. methyl or isopropyl groups, preferably methyl groups. The free bond of the bi- or the tricyclic radical can be located in any desired position in the molecule; the radical can thus be bonded via a bridgehead atom or an atom in a bridge. The free bond can also be located in any desired stereochemical position, for example in an exo- or an endo-position.

Examples of 6-membered aromatic ring system include phenyl, pyridyl, pyridazinyl, pyrimidinyl, pyrazinyl, 1,3,5-triazinyl, 1,2,4-triazinyl, 1,2,3-triazinyl, tetrazinyl.

Examples of parent substances of bicyclic ring systems include norbornane (=bicyclo[2.2.1]heptane), bicyclo[2.2.2]octane and bicyclo[3.2.1]octane. An example of a system substituted by an oxo group is camphor (=1,7,7-trimethyl-2-oxobicyclo[2.2.1]heptane).

Examples of parent substances of tricyclic systems include twistane (=tricyclo[4.4.0.0$^{3,8}$]decane), adamantane (=tricyclo[3.3.1.1$^{3,7}$]decane), noradamantane (=tricyclo[3.3.1.0$^{3,7}$]nonane), tricyclo[2.2.1.0$^{2,6}$]heptane, tricyclo[5.3.2.0$^{4,9}$]dodecane, tricyclo[5.4.0.0$^{2,8}$]undecane or tricyclo-[5.5.1.0$^{3,11}$]tridecane.

Aryl is, for example, phenyl, naphthyl, biphenylyl, anthryl or fluorenyl, 1-naphthyl, 2-naphthyl and in particular phenyl being preferred. Aryl radicals, in particular phenyl radicals, can be mono- or polysubstituted, preferably mono-, di- or trisubstituted, by identical or different radicals from the group consisting of $(C_1-C_8)$-alkyl, in particular $(C_1-C_4)$-alkyl, $(C_1-C_8)$-alkoxy, in particular $(C_1-C_4)$-alkoxy, halogen, such as fluorine, chlorine and bromine, nitro, amino, trifluoromethyl, hydroxyl, methylenedioxy, cyano, hydroxycarbonyl, aminocarbonyl, $(C_1-C_4)$-alkoxycarbonyl, phenyl, phenoxy, benzyl, benzyloxy, tetrazolyl, $(R^{17}O)_2P(O)$— and $(R^{17}O)_2P(O)$—O—, where $R^{17}$ is H, $(C_1-C_{10})$-alkyl, $(C_6-C_{14})$-aryl or $(C_6-C_{14})$-aryl-$(C_1-C_8)$-alkyl.

In monosubstituted phenyl radicals, the substituent can suitably be located in the 2- , the 3- or the 4-position, with the 3- and the 4-position being preferred. If phenyl is disubstituted, the substituents can be in the 1,2-, 1,3- or 1,4-position relative to one another. Preferably, in disubstituted phenyl radicals the two substituents are arranged in the 3- and the 4-position, relative to the linkage site.

Aryl groups may furthermore be mono- or polycyclic aromatic ring systems in which 1 to 5 carbon atoms can be replaced by 1 to 5 heteroatoms, such as, for example, 2-pyridyl, 3-pyridyl, 4-pyridyl, pyrrolyl, furyl, thienyl, imidazolyl, pyrazolyl, oxazolyl, isoxazolyl, thiazolyl, isothiazolyl, tetrazolyl, pyridyl, pyrazinyl, pyrimidinyl, indolyl, isoindolyl, indazolyl, phthalazinyl, quinolyl, isoquinolyl, quinoxalinyl, quinazolinyl, cinnolinyl, β-carbolinyl, or a benzo-fused, cyclopenta-, cyclohexa- or cyclohepta-fused derivative of these radicals.

These heterocycles can be substituted by the same substituents as the abovementioned carbocyclic aryl systems.

In the series of these aryl groups, mono- or bicyclic aromatic ring systems having 1–3 heteroatoms from the group consisting of N, O, S, are preferred, which can be substituted by 1–3 substituents from the group consisting of $(C_1-C_6)$-alkyl, $(C_1-C_6)$-alkoxy, fluorine, Cl, $NO_2$, $NH_2$, trifluoromethyl, OH, $(C_1-C_4)$-alkoxycarbonyl, phenyl, phenoxy, benzyloxy or benzyl.

Particularly preferred in this case are mono- or bicyclic aromatic 5–10-membered ring systems having 1–3 heteroatoms from the series N, O, S, which can be substituted by 1–2 substituents from the group consisting of $(C_1-C_4)$-alkyl, $(C_1-C_4)$-alkoxy, phenyl, phenoxy, benzyl or benzyloxy.

Also preferred are compounds of the formula I which carry a lipophilic radical $R^4$, $R^5$, $R^6$ or $R^7$ such as, for example, benzyloxycarbonylamino, cyclohexylmethylcarbonylamino, etc.

L- or D-amino acids can be natural or unnatural amino acids. α-Amino acids are preferred. Examples which may be mentioned are: (cf. Houben-Weyl, Methoden der organischen Chemie [Methods of Organic Chemistry], Volume XV/1 and 2, Georg Thieme Verlag, Stuttgart, 1974): This reference and all its editions referred to in this disclosure are hereby incorporated by reference in their entireties.

Aad, Abu, γAbu, γBz, 2ABz, εAca, Ach, Acp, Adpd, Ahb, Aib, βAib, Ala, βAla, ΔAla, Alg, All, Ama, Amt, Ape, Apm, Apr, Arg, Asn, Asp, Asu, Aze, Azi, Bai, Bph, Can, Cit, Cys, (Cys)$_2$, Cyta, Daad, Dab, Dadd, Dap, Dapm, Dasu, Djen, Dpa, Dtc, Fel, Gin, Glu, Gly, Guv, hAla, hArg, hCys, hGln, hglu, His, hIle, hLeu, hLys, hMet, hPhe, hPro, hSer, hThr, hTrp, hTyr, Hyl, Hyp, 3Hyp, lie, Ise, Iva, Kyn, Lant, Lcn, Leu, Lsg, Lys, βLys, ΔLys, Met, Mim, Min, nArg, Nle, Nva, Oly, Orn, Pan, Pec, Pen, Phe, Phg, Pic, Pro, ΔPro, Pse, Pya, Pyr, Pza, Qin, Ros, Sar, Sec, Sem, Ser, Thi, βThi, Thr, Thy, Thx, Tia, Tle, Tly, Trp, Trta, Tyr, Val, tert-butylglycine (Tbg), neopentylglycine (Npg), cyclohexylglycine (Chg), cyclohexylalanine (Cha), 2-thienylalanine (Thia), 2,2-diphenylaminoacetic acid, 2-(p-tolyl)-2-phenylaminoacetic acid, 2-(p-chlorophenyl)aminoacetic acid.

The amino acids can furthermore include: pyrrolidine-2-carboxylic acid; piperidine-2carboxylic acid; 1,2,3,4-tetrahydroisoquinoline-3-carboxylic acid; decahydroisoquinoline-3-carboxylic acid; octahydroindole-2-carboxylic acid; decahydroquinoline-2-carboxylic acid; octahydrocyclopenta[b]pyrrole-2-carboxylic acid; 2-azabicyclo[2.2.2]octane-3-carboxylic acid; 2-azabicyclo[2.2.1]heptane-3-carboxylic acid; 2-azabicyclo[3.1.0]hexane-3-carboxylic acid; 2-azaspiro[4.4]nonane-3-carboxylic acid; 2-azaspiro[4.5]decane-3-carboxylic acid; spiro(bicyclo[2.2.1]heptane)-2,3-pyrrolidine-5-carboxylic acid; spiro(bicyclo[2.2.2]octane)-2,3-pyrrolidine-5-carboxylic acid; 2-azatricyclo[4.3.0.1$^{6,9}$]decane-3-carboxylic acid; decahydrocyclo-hepta[b]pyrrole-2-carboxylic acid; decahydrocyclooctа[c]pyrrole-2-carboxylic acid; octahydrocyclopenta[c]pyrrole-2-carboxylic acid; octahydroisoindole-1-carboxylic acid; 2,3,3a,4,6a-hexahydrocyclopenta[b]pyrrole-2-carboxylic acid; 2,3,3a,4,5,7a-hexahydroindole-2-carboxylic acid; tetrahydrothiazole-4-carboxylic acid; isoxazolidine-3-carboxylic acid; pyrazolidine-3-carboxylic acid, hydroxypyrrolidine-2-carboxylic acid, all of which can be optionally substituted (see following formulae):

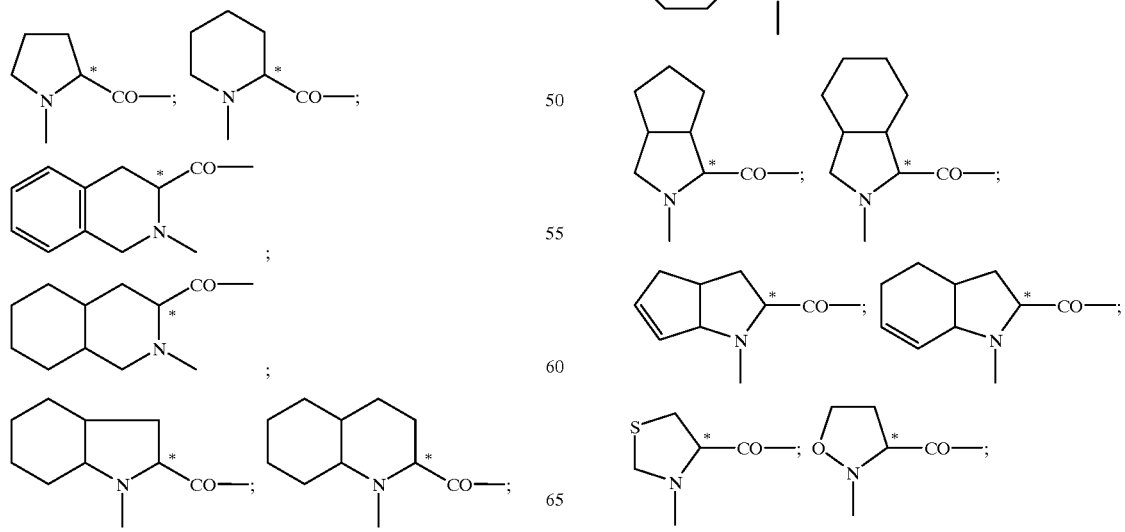

-continued

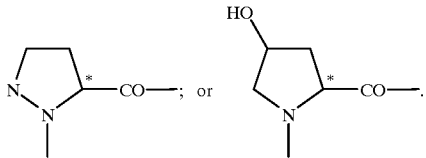

The heterocycles on which the abovementioned radicals are based are disclosed, for example, in U.S. Pat. No. 4,344,949; U.S. Pat. No. 4,374,847; U.S. Pat. No. 4,350,704; EP-A 29,488; EP-A 31,741; EP-A 46,953; EP-A 49,605; EP-A 49,658; EP-A 50,800; EP-A 51,020; EP-A 52,870; EP-A 79,022; EP-A 84,164; EP-A 89,637; EP-A 90,341; EP-A 90,362; EP-A 105,102; EP-A 109,020; EP-A 111,873; EP-A 271,865 and EP-A 344,682 all of which are incorporated herein by reference in their entireties. p The amino acids can furthermore also be present as esters or amides, such as, for example, the methyl ester, ethyl ester, isopropyl ester, isobutyl ester, tert-butyl ester, benzyl ester, ethyl amide, semicarbazide or ω-amino-$(C_2$–$C_8)$-alkyl amide.

Functional groups of the amino acids can be present in protected form. Suitable protective groups such as, for example, urethane protective groups, carboxyl protective groups and side chain protective groups are described in Hubbuch, Kontakte (Merck) 1979, No. 3, pages 14 to 23 and in Bullesbach, Kontakte (Merck) 1980, No. 1, pages 23 to 35 both of which are incorporated by reference in their entireties. The following may be mentioned in particular: Aloc, Pyoc, Fmoc, Tcboc, Z, Boc, Ddz, Bpoc, Adoc, Msc, Moc, Z($NO_2$), Z(Haln), Bobz, Iboc, Adpoc, Mboc, Acm, tert-Butyl, OBzI, ONbzI, OMbzI, BzI, Mob, Pic, Trt.

Physiologically tolerable salts of the compounds of the formula I are, in particular, pharmaceutically utilizable or nontoxic salts. Such salts are formed, for example, from compounds of the formula I which contain acidic groups, e.g. carboxyl, with alkali metals or alkaline earth metals, such as, for example, Na, K, Mg and Ca, and with physiologically tolerable organic amines, such as, for example, triethylamine, ethanolamine or tris-(2-hydroxyethyl) amine. Compounds of the formula I which contain basic groups, e.g. an amino group, an amidino group or a guanidino group, form salts with inorganic acids, such as, for example, hydrochloric acid, sulfuric acid or phosphoric acid, and with organic carboxylic or sulfonic acids, such as, for example, acetic acid, citric acid, benzoic acid, maleic acid, fumaric acid, tartaric acid, methanesulfonic acid or p-toluenesulfonic acid.

The compounds of the formula I according to the invention can contain optically active carbon atoms which independently of one another can have R or S configuration and can thus be present in the form of pure enantiomers or pure diastereomers or in the form of enantiomer mixtures or diastereomer mixtures. The present invention relates both to pure enantiomers and enantiomer mixtures and to diastereomers and diastereomer mixtures. The invention covers mixtures of two stereoisomers and of more than two stereoisomers of the formula I and all ratios of stereoisomers in the mixtures.

Since at least one of the radicals A, D or F independently of one another is —$NR^2$—$N$=$CR^2$—, —$N$=$CR^2$— or —$R^2C$=$N$—, and if one or more radicals of the formula I is/are —$CR^2$=$CR^3$—, the compounds of the formula I according to the invention can be present as E/Z isomer mixtures. The present invention relates to both pure E and Z isomers and to mixtures of E/Z isomer in all ratios.

Diastereomers, including E/Z isomers, can be separated into the individual isomers by chromatography. Racemates can either be separated into the two enantiomers by chromatography on chiral phases or by resolution.

The compounds of the formula I according to the invention can moreover contain mobile hydrogen atoms, i.e. be present in various tautomeric forms. The present invention also relates to these tautomers.

Preferred compounds of the formula I are those in which:

A is a direct bond, $(C_1$–$C_6)$-alkanediyl, —$NR^2$—$N$=$CR^2$—, —$NR^2$—$C(O)$—$NR^2$—, —$NR^2$—$C(O)$O—, —$NR^2$—$C(O)S$—, —$NR^2$—$C(S)$—$NR^2$—, —$NR^2$—$C(S)$—$O$—, —$NR^2$—$C(S)$—$S$—, —$NR^2$—$S(O)_n$—$NR^2$—, —$NR^2$—$S(O)_n$—$O$—, —$NR^2$—$S(O)_n$—, $(C_3$–$C_8)$-cycloalkanediyl, —$C$≡$C$—, —$NR^2$—$C(O)$—, —$C(O)$—$NR^2$—, —$(C_5$–$C_{12})$-arylene—$C(O)$—$NR^2$—, —$O$—, —$S(O)_n$—, —$(C_5$–$C_{12})$-arylene—, —$CO$—, —$(C_5$–$Cl_2)$-arylene—$CO$—, —$NR^2$—, —$SO_2$—$NR^2$—, —$CO_2$—, —$N$=$CR^2$—, —$R^2C$=$N$—, —$CR^2$=$CR^3$—, —$(C_5$–$Cl_2)$-arylene—$S(O)_n$—, which in each case can be mono- or disubstituted by $(C_1$–$C_8)$-alkanediyl;

B is a direct bond, $(C_1$–$C_8)$-alkanediyl, —$CR^2$=$CR^3$— or —$C$≡$C$—, which in each case can be mono- or disubstituted by $(C_1$–$C_8)$-alkanediyl;

D is a direct bond, $(C_1$–$C_8)$-alkanediyl or —$O$—, —$NR^2$—, —$CO$—$NR^2$—, —$NR^2CO$—, —$NR^2$—$C(O)$—$NR^2$—, —$NR^2$—$C(S)$—$NR^2$—, —$OC(O)$—, —$C(O)O$—, —$CO$—, —$CS$—, —$S(O)$—, —$S(O)_2$—, —$S(O)_2$—$NR^2$—, —$NR^2$—$S(O)$—, —$NR^2$—$S(O)_2$—, —$S$—, —$CR^2$=$CR^3$—, —$C$—$C$—, —$NR^2$—$N$=$CR^2$—, —$N$=$CR^2$ or —$R^2C$=$N$—, which in each case can be mono- or disubstituted by $(C_1$–$C_6)$-alkanediyl;

E is a 6-membered aromatic ring system, which optionally contains 1 or 2 nitrogen atoms and is optionally substituted by 1–3 identical or different radicals from the group consisting of $R^2$, $R^3$, fluorine, Cl and OH;

F is defined as D;

G is 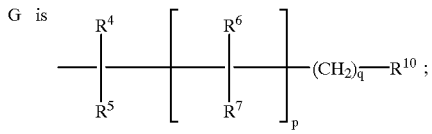

Y is a direct bond or —$NR^2$—;

$R^1$ is $R^2$—$C(=NR^2)$—$NR^3$—, $R^2R^3N$—$C(=NR^2)$—, $R^2R^3N$—$C(=NR^2)$—$NR^2$—, or a 4–10-membered mono- or polycyclic aromatic or nonaromatic ring system which can optionally contain 1–4 heteroatoms from the group consisting of N, O and S and can optionally be monosubstituted or polysubstituted by substituents from the group consisting of $R^{12}$, $R^{13}$, $R^{14}$ and $R^{15}$;

$R^2$, $R^3$ independently of one another are H, $(C_1$–$C_8)$-alkyl which is optionally mono- or polysubstituted by fluorine, $(C_3$–$C_8)$-cycloalkyl, $(C_3$–$C_8)$-cycloalkyl-$(C_1$–$C_6)$-alkanediyl, $(C_5$–$C_{12})$-aryl, $(C_5$–$C_{12})$-aryl-$(C_1$–$C_6)$-alkanediyl, $H_2N$, $(R^8O)R^8NR^9$, $R^8OR^9$, $R^8OC(O)R^9$, $R^8$—$(C_5$–$C_{12})$-arylene-$R^9$, $R^8R^8NR^9$, HO—$(C_1$–$C_8)$-alkanediyl—$NR^8R^9$, $R^8R^8NC(O)R^9$, $R^8C(O)NR^8R^9$, $R^8C(O)R^9$, $R^8R^8N$—$C(=NR^8)$—, $R^8R^8N$—$C(=NR^8)$—$NR^8$— or $(C_1$–$C_{10})$-alkylcarbonyloxy-$(C_1$–$C_4)$-alkanediyloxycarbonyl;

$R^4$, $R^5$, $R^6$, $R^7$ independently of one another are H, fluorine, OH, $(C_1-C_8)$-alkyl, $(C_3-C_8)$-cycloalkyl, $(C_3-C_8)$-cycloalkyl-$(C_1-C_8)$-alkanediyl, or $R^8OR^9$, $R^8SR^9$, $R^8CO_2R^9$, $R^8OC(O)R^9$, $R^8$—$(C_5-C_{12})$-arylene-$R^9$, $R^8N(R^2)R^9$, $R^8R^8NR^9$, $R^8N(R^2)C(O)OR^9$, $R^8S(O) N(R^2)R^9$, $R^8OC(O)N(R^2)R^9$, $R^8C(O)N(R^2)R^9$, $R^8N(R^2)C(O)N(R^2)R^9$, $R^8N(R^2)S(O)_nN(R^2)R^9$, $R^8S(O)_nR^9$, $R^8SC(O)N(R^2)R^9$, $R^8C(O)R^9$, $R^8N(R^2)C(O)R^9$, $R^8N(R^2)S(O)_nR^9$;

$R^8$ is H, $(C_1-C_6)$-alkyl, $(C_3-C_8)$-cycloalkyl, $(C_3-C_8)$-cycloalkyl-$(C_1-C_6)$-alkanediyl, $(C_5-C_{12})$-aryl, $(C_5-C_{12})$-aryl-$(C_1-C_6)$-alkanediyl, it being possible for the alkyl radicals to be mono- or polysubstituted by fluorine;

$R^9$ is a direct bond or $(C_1-C_6)$-alkanediyl;

$R^{10}$ is $C(O)R^{11}$, $C(S)R^{11}$, $S(O)_nR^{11}$, $P(O)(R^{11})_n$ or a four to eight-membered, saturated or unsaturated heterocycle which contains 1, 2, 3 or 4 heteroatoms from the group consisting of N, O, S;

$R^{11}$ is OH, $(C_1-C_6)$-alkoxy, $(C_5-C_{12})$-aryl-$(C_1-C_6)$-alkanediyloxy, $(C_5-C_{12})$-aryloxy, $(C_1-C_6)$-alkylcarbonyloxy-$(C_1-C_4)$-alkanediyloxy, $(C_5-C_{12})$-aryl-$(C_1-C_6)$-alkanediylcarbonyloxy-$(C_1-C_6)$-alkanediyloxy, $NH_2$, mono- or di-$(C_1-C_6$-alkyl)-amino, $(C_5-C_{12})$-aryl-$(C_1-C_6)$-alkanediylamino, $(C_1-C_6)$-dialkylaminocarbonylmethylenoxy;

$R^{12}$, $R^{13}$, $R^{14}$, $R^{15}$ independently of one another are H, $(C_1-C_8)$-alkyl, which is optionally mono- or polysubstituted by fluorine, $(C_3-C_8)$-cycloalkyl, $(C_3-C_8)$-cycloalkyl-$(C_1-C_6)$-alkanediyl, $(C_5-C_{12})$-aryl, $(C_5-C_{12})$-aryl-$(C_1-C_6)$-alkanediyl, $H_2N$, $(R^8O)R^3NR^9$, $R^8OR^9$, $R^8OC(O)R^9$, $R^8$—$(C_5-C_{12})$-arylene-$R^9$, $R^8R^8NR^9$, HO—$(C_1-C_8)$-alkylanedi-$N(R^2)R^9$, $R^8N(R^2)C(O)R^9$, $R^8C(O)N(R^2)R^9$, $R^8C(O)R^7$, $R^2R^3N$—$C(=NR^2)$—, $R^2R^3N$—$C(=NR^3)$—$NR^2$—, =O, =S;

n is 1 or 2;

p, q independently of one another are 0 or 1;

in all their stereoisomeric forms and mixtures thereof in any ratio;

and their physiologically tolerable salts.

Particularly preferred compounds of the formula I are those in which:

A is a direct bond, $(C_1-C_6)$-alkanediyl, —$NR^2$—N=$CR^2$—, —$NR^2$—C(O)—, —C(O)—$NR^2$—, —$(C_5-C_{10})$-arylene-, —CO—, —$NR^2$—, —$CO_2$—, —N=$CR^2$—, —$R^2C$=N—, —$CR^2$=$CR^3$—, which in each case can be mono- or disubstituted by $(C_1-C_6)$-alkanediyl;

B is a direct bond, $(C_1-C_6)$-alkanediyl, —$CR^2$=$CR^3$—, which can be mono- or disubstituted by $(C_1-C_6)$-alkanediyl;

D is a direct bond, $(C_1-C_6)$-alkanediyl, —O—, —$NR^2$—, —$NR^2$—CO—, —C(O)—$NR^2$—, —$NR^2$—C(O)—$NR^2$—, —$NR^2$—C(S)—$NR^2$—, —OC(O)—, —C(O)—, —$CR^2$=$CR^3$—, —$NR^2$—$S(O)_2$—, —N=$CR^2$— or —$R^2C$=N—, which in each case can be mono- or disubstituted by $(C_1-C_6)$-alkanediyl;

E is phenylene or pyridinediyl which is optionally substituted by 1–3 identical or different radicals from the group consisting of $R^2$ and $R^3$;

F is a direct bond, $(C_1-C_6)$-alkanediyl, —O—, —CO—$NR^2$, —$NR^2$—CO—, —$NR^2$—C(O)—$NR^2$—, —OC(O)—, —C(O)O—, —CO—, —$S(O)_2$—, —$S(O)_2$—$NR^2$—, —$NR^2$—$S(O)_2$—, —$CR^2$=$CR^3$—, —C≡C—, which in each case can be mono- or disubstituted by $(C_1-C_6)$-alkanediyl;

G is 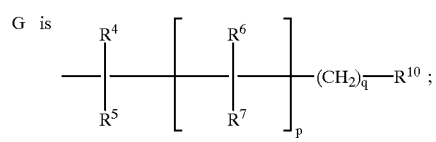

Y is a direct bond or —NH—;

$R^1$ is $R^2$—C(=$NR^2$)—$NR^2$—, $R^2R^3N$—C(=$NR^2$)—,

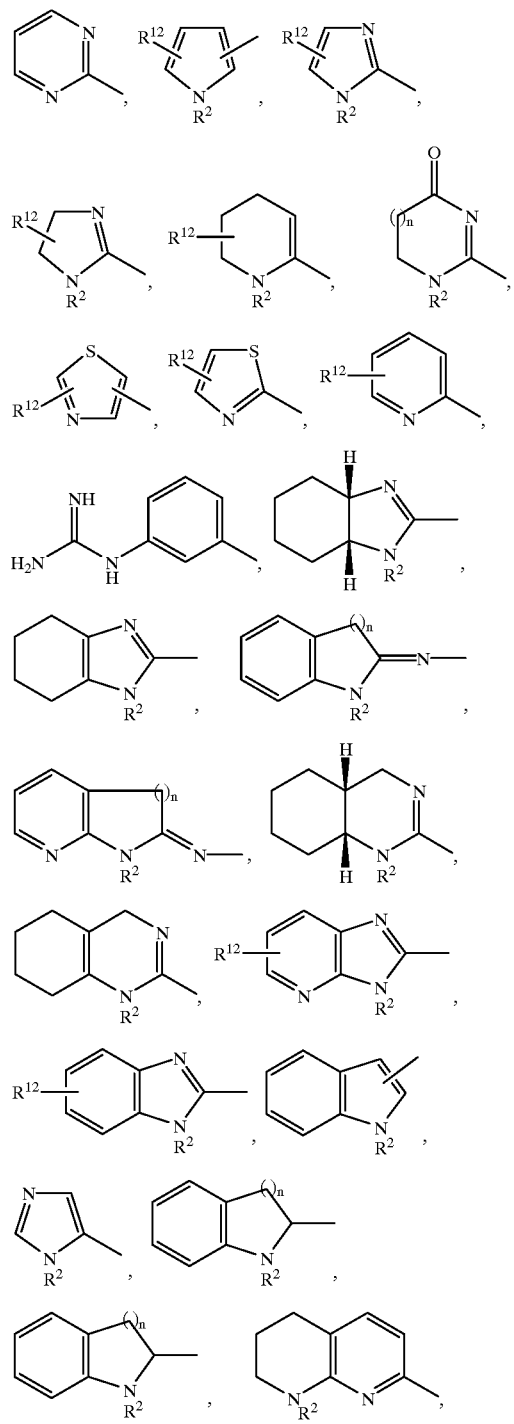

-continued

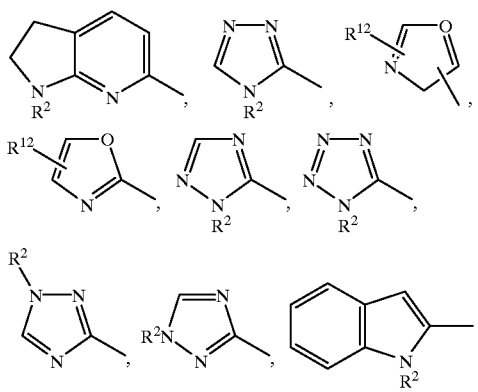

R², R³ independently of one another are H, (C₁–C₆)-alkyl, which is optionally mono- or polysubstituted, preferably 1–6 times, by fluorine, (C₃–C₆)-cycloalkyl, (C₃–C₆)-cycloalkyl-(C₁–C₄)-alkanediyl, (C₅–C₁₀)-aryl, (C₅–C₁₀)-aryl-(C₁–C₄)-alkanediyl, H₂N, R⁸OR⁹, R⁸R⁸NR⁹, R⁸NHC(O)R⁹, H₂N—C(═NH)—, H₂N—C(═NH)—NH—;

R⁴, R⁵, R⁶, R⁷ independently of one another are H, fluorine, OH, (C₁–C₆)-alkyl, (C₃–C₆)-cycloalkyl, (C₃–C₆)-cycloalkyl-(C₁–C₆)-alkanediyl, or R⁸OR⁹, R⁸CO₂R⁹, R⁸OC(O)R⁹, R⁸—(C₅–C₁₀)-arylene-R⁹, R⁸NHR⁹, R⁸R⁸NR⁹, R⁸NHC(O)OR⁹, R⁸S(O)ₙNHR⁹, R⁸OC(O)NHR⁹, R⁸C(O)NHR⁹, R⁸C(O)R⁹, R⁸NHC(O)NHR⁹, R⁸NHS(O)ₙNHR⁹, R⁸NHC(O)R⁹, R⁸NHS(O)ₙR⁹;

R⁸ is H, (C₁–C₆)-alkyl, (C₃–C₆)-cycloalkyl, (C₃–C₆)-cycloalkyl-(C₁–C₄)-alkanediyl, (C₅–C₁₀)-aryl, (C₅–C₁₀)-aryl-(C₁–C₄)-alkanediyl, it being possible for the alkyl radicals to be substituted by 1–6-fluorine atoms;

R⁹ is a direct bond or (C₁–C₆)-alkanediyl;

R¹⁰ is C(O)R¹¹;

R¹¹ is OH, (C₁–C₆)-alkoxy, (C₅–C₁₀)-aryl-(C₁–C₆)-alkanediyloxy, (C₅–C₁₀)-aryloxy, (C₁–C₆)-alkylcarbonyloxy-(C₁–C₄)-alkanediyloxy, (C₅–C₁₀)-aryl-(C₁–C₄)-alkanediylcarbonyloxy-(C₁–C₄)-alkanediyloxy, NH₂, mono- or di-(C₁–C₆-alkyl)-amino;

R¹² is H, (C₁–C₆)-alkyl which is optionally mono- or polysubstituted by fluorine, (C₃–C₆)-cycloalkyl, (C₃–C₆)-cycloalkyl-(C₁–C₄)-alkanediyl, (C₅–C₁₀)-aryl, (C₅–C₁₀)-aryl-(C₁–C₄)-alkanediyl, H₂N, R⁸OR⁹, R⁸OC(O)R⁹, R⁸—(C₅–C₁₀)-arylene-R⁹, R⁸R⁸NR⁹, R⁸NHC(O)R⁹, R⁸C(O)NHR⁹, H₂N—C(═NH)—, H₂₂N—C(═NH)—NH—, ═O;

n is 1 or 2;

p, q independently of one another are 0 or 1;

in all their stereoisomeric forms and mixtures thereof in any ratio;

and their physiologically tolerable salts.

Very particularly preferred compounds of the formula I are those in which:

A is a direct bond, —NR²—N═CR²— or —N═CR²—;

B is a direct bond or (C₁–C₆)-alkanediyl;

D is a direct bond, (C₁–C₄)-alkanediyl or —O—, —NR²—, —NR²—CO—, —C(O)—NR²—, —NR²—C(O)—NR²—, —N═CR²— or —R²C═N—, which in each case can be mono- or disubstituted by (C₁–C₆)-alkanediyl;

E is phenylene or pyridinediyl, which is optionally substituted by 1 or 2 radicals from the group consisting of R², R³;

F is a direct bond, (C₁–C₆)-alkanediyl, or —O—, —CO—NR²—, —NR²—CO—, —NR²—C(O)—NR²—, —CR²═CR³— or —C≡C—, which in each case can be mono- or disubstituted by (C₁–C₄)-alkanediyl;

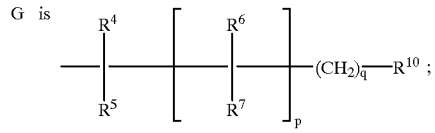

Y is a direct bond or —NH—;

R¹ is R²R³N—C(═NR²)—,

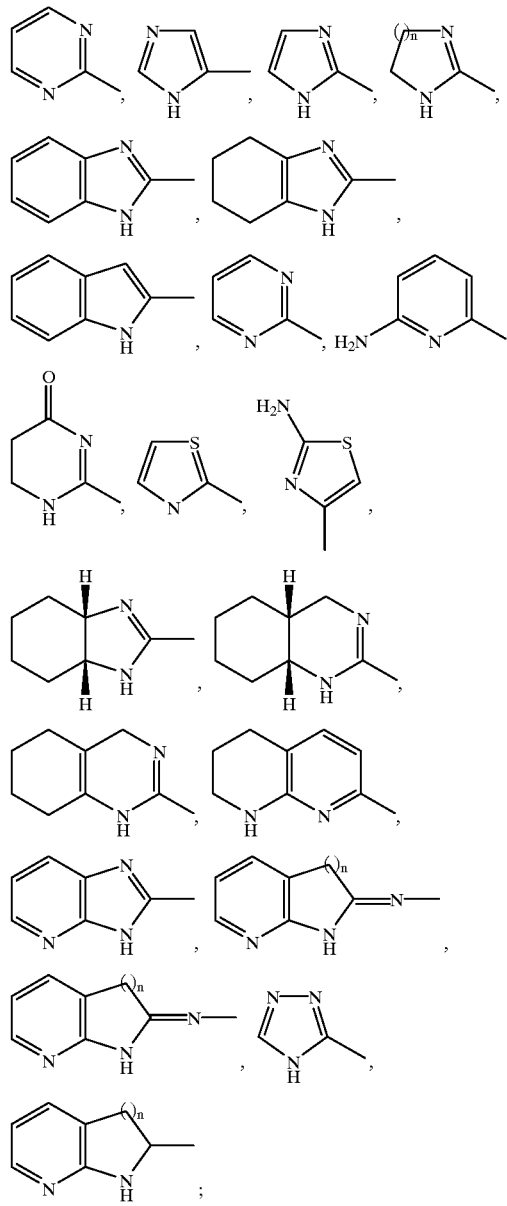

R², R³ independently of one another are H,(C₁–C₆)-alkyl, trifluoromethyl, pentafluoroethyl, (C₅–C₆)-cycloalkyl, ($C_5$–$C_6$)-cycloalkyl-($C_1$–$C_2$)-alkanediyl, phenyl, benzyl, $H_2N$, $R^8OR^9$, $R^8NHR^9$, $R^8R^8NR^9$, $R^8NHC(O)R^9$, $H_2N$—C(=NH)—, $H_2N$—C(=NH)—NH—;

$R^4$, $R^5$, $R^6$, $R^7$ independently of one another are H, fluorine, OH, ($C_1$–$C_6$)-alkyl, ($C_5$–$C_6$)-cycloalkyl, ($C_5$–$C_6$)-cycloalkyl-($C_1$–$C_6$)-alkanediyl, or $R^8OR^9$, $R^8$—($C_5$–$C_{10}$)-arylene-$R^9$, $R^8R^8NR^9$, $R^8NHC(O)OR^9$, $R^8S(O)_nNHR^9$, $R^8OC(O)NHR^9$, $R^8C(O)NHR^9$;

$R^8$ is H, ($C_1$–$C_6$)-alkyl, ($C_5$–$C_6$)-cycloalkyl, ($C_5$–$C_6$)-cycloalkyl-($C_1$–$C_2$)-alkanediyl, ($C_5$–$C_6$)-aryl, ($C_5$–$C_6$)-aryl-($C_1$–$C_2$)-alkanediyl;

$R^9$ is a direct bond or ($C_1$–$C_6$)-alkanediyl;

$R^{10}$ is $C(O)R^{11}$;

$R^{11}$ is OH, ($C_1$–$C_6$)-alkoxy, phenoxy, benzyloxy, ($C_1$–$C_4$)-alkylcarbonyloxy-($C_1$–$C_4$)-alkanediyloxy, $NH_2$, mono- or di-($C_1$–$C_6$-alkyl)-amino;

n is 1 or 2;

p, q independently of one another are 0 or 1;

in all their stereoisomeric forms and mixtures thereof in any ratio;

and their physiologically tolerable salts.

Compounds of the formula I can generally be prepared, for example in the course of a convergent synthesis, by linkage of two or more fragments which can be derived retrosynthetically from the formula I. In the preparation of the compounds of the formula I, it may generally be necessary in the course of the synthesis temporarily to block functional groups which could lead to undesired reactions or side reactions in the respective synthesis step by means of a protective group strategy suited to the synthesis problem and known to the person skilled in the art using the present specification as a guide. The method of fragment coupling is not restricted to the following examples, but is generally applicable for syntheses of the compounds of the formula I.

For example, compounds of the formula I of the type

where F in the formula I is —C(O)NR$^2$— can be prepared by condensation of a compound of the formula II

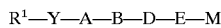   II, where M is hydroxycarbonyl, ($C_1$–$C_6$)-alkoxycarbonyl, activated carboxylic acid derivatives such as acid chlorides, active esters or mixed anhydrides, with HNR$^2$—G.

For the condensation of two fragments with formation of an amide bond, the coupling methods of peptide chemistry known per se (see, for example, Houben-Weyl, Methoden der Organischen Chemie [Methods of Organic Chemistry], Volume 1511 and 1512, Georg Thieme Verlag, Stuttgart, 1974) are advantageously used. For this purpose, as a rule it is necessary to protect nonreacting amino groups present during the condensation by reversible protective groups. The same applies to carboxyl groups not participating in the reaction, which are preferably employed as ($C_1$–$C_6$)-alkyl, benzyl or tert-butyl esters. Amino group protection is unnecessary if the amino groups to be generated are still present as nitro or cyano groups and are formed by hydrogenation only after coupling. After coupling, the protective groups present are removed in a suitable manner. For example, $NO_2$ groups (guanidino protection), benzyloxycarbonyl groups and benzyl esters can be removed by hydrogenation. The protective groups of the tert-butyl type are removed under acidic conditions, while the 9-fluorenylmethyloxycarbonyl radical is removed by secondary amines. Compounds of the formula I in which $R^1$ has the meaning indicated, Y is —NR$^2$— and A is —C(O)— can be prepared, for example, by the generally known coupling methods of peptide chemistry by coupling $R^1$—NR$^2$H with HO$_2$C—B—D—E—F—G.

Compounds of the formula I in which $R^1$—Y—A— is

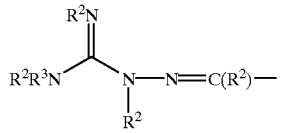

or cyclic guanylhydrazones of the type

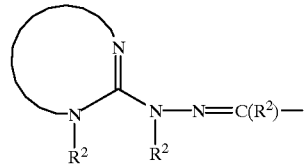

are prepared, for example, by condensation of

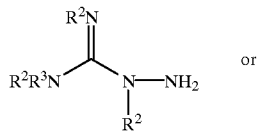

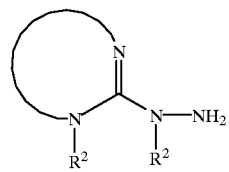

with ketones or aldehydes of the type O=C(R$^2$)— or corresponding acetals or ketals according to customary literature processes, for example analogously to N. Desideri et at., Arch. Pharm. 325 (1992) 773–777, A. Alves et al., Eur. J. Med. Chem. Chim. Ther. 21 (1986) 297–304, D. Heber et al.; Pharmazie 50 (1995) 663–667, T. P. Wunz et al., J. Med. Chem. 30 (1987) 1313–1321, K.-H. Buchheit et al., J. Med. Chem. 38 (1995), 2331–2338, all incorporated herein by references in their entireties, or as described in Example 1 (condensation with hydrochloric acid catalysis in glacial acetic acid).

The above guanylhydrazones may be obtained as E/Z isomer mixtures, which can be separated according to customary chromatographic processes.

Compounds of the formula I in which $R^1$—Y—A— is $R^2$—C(=NR$^2$)—NR$^2$—N=C(R$^2$)— or a system comprising a mono- or polycycle of the type

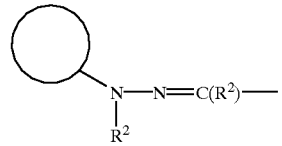

can be obtained analogously.

Compounds of the formula I in which D is —N=C(R$^2$)— are obtained, for example, by condensation of ketones or aldehydes of the type O=C(R²)—E—F—G with amines of the type R¹—Y—A—B—NH₂ according to customary literature processes (see, for example, J. March, Advanced Organic Chemistry, Third Edition, John Wiley & Sons, 1985, p. 796 et seq.) which is incorporated herein by references in its entirety. Compounds of the formula I in which D is —R²C=N— can be obtained analogously, for example, by condensation of ketones or aldehydes of the type R¹—Y—A—B—C(R²)=O with amines of the type H₂N—E—F—G.

Compounds of the formula I in which F is —N=C(R²)— or —R²C=N— can be prepared as described above for compounds of the formula I in which D is —N=C(R²)— or —R²C=N—.

Compounds of the formula I where $R^{10}$=SO₂R¹¹ are prepared, for example, by oxidizing compounds of the formula I where $R^{10}$=SH by processes known from the literature (cf. Houben-Weyl, Methoden der Organischen Chemie [Methods of Organic Chemistry], Vol. E12/2, Georg Thieme Verlag, Stuttgart 1985, p. 1058 et seq.) to compounds of the formula I where $R^{10}$=SO₃H, from which the compounds of the formula I where $R^{10}$=SO₂R¹¹(R¹¹≈OH) are then prepared directly or via corresponding sulfonic acid halides by esterification or linkage of an amide bond. Oxidation-sensitive groups in the molecule, such as, for example, amino, amidino or guanidino groups are protected, if necessary, by suitable protective groups before carrying out the oxidation.

Compounds of the formula I where $R^{10}$=S(O)R¹¹ are prepared, for example, by converting compounds of the formula I where $R^{10}$=SH into the corresponding sulfide ($R^{10}$=S⁻) and then oxidizing with meta-chloroperbenzoic acid to the sulfinic acids ($R^{10}$=SO₂H) (cf. Houben-Weyl, Methoden der Organischen Chemie [Methods of Organic Chemistry], Vol. E1/1, Georg Thieme Verlag, Stuttgart 1985, p. 618 et seq.), from which the corresponding sulfinic acid esters or amides $R^{10}$=S(O)R¹¹ (R¹¹≈OH) can be prepared by methods known from the literature. Generally, other methods known from the literature can also be used for the preparation of compounds of the formula I where $R^{11}$=S(O)ₙR¹¹ (n=1, 2) (cf. Houben-Weyl, Methoden der Organischen Chemie [Methods of Organic Chemistry], Vol. E11/1, Georg Thieme Verlag, Stuttgart 1985, p. 618 et seq. or Vol. E11/2, Stuttgart 1985, p. 1055 et seq.).

Compounds of the formula I where $R^{10}$=P(O)(R¹¹)ₙ (n=1, 2) are synthesized from suitable precursors by processes known from the literature (cf. Houben-Weyl, Methoden der Organischen Chemie [Methods of Organic Chemistry], Vol. E1 and E2, Georg Thieme Verlag, Stuttgart 1982), the synthesis method selected being suited to the target molecule.

Compounds of the formula I where $R^{10}$=C(S)R¹¹ can be prepared by processes known from the literature (cf. Houben-Weyl, Methoden der Organischen Chemie [Methods of Organic Chemistry], Vol. E5/1 and E5/2, Georg Thieme Verlag, Stuttgart 1985).

Compounds of the formula I where $R^{10}$=S(O)ₙR¹¹ (n=1, 2), P(O)(R¹¹)ₙ(n=1, 2) or C(S)R¹¹ can of course also be prepared by fragment coupling, such as described above, which is advisable, for example, when, for example, a (commercially available) aminosulfonic acid, aminosulfinic acid, aminophosphonic acid or aminophosphinic acid or derivatives derived therefrom, such as esters or amides, are contained in F—G of the formula 1.

Compounds of the formula I in which R¹—Y—A— is

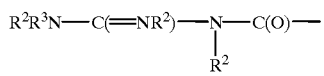

or cyclic acylguanidines of the type

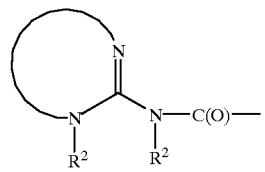

can be prepared, for example, by reacting a compound of the formula III

   III in which Q is an easily nucleophilically substitutable leaving group, with the appropriate guanidine (derivative) of the type

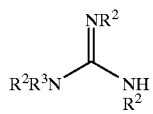

or the cyclic guanidine (derivative) of the type

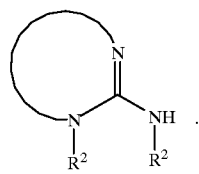

The above activated acid derivatives of the formula III, in which Q is an alkoxy group, preferably a methoxy group, a phenoxy group, a phenylthio, methylthio, 2-pyridylthio group, a nitrogen heterocycle, preferably 1-imidazolyl, are advantageously obtained in a manner known per se from the carboxylic acids (Q=OH) or carbonyl chlorides (Q=Cl) on which they are based. The latter are in turn obtained in a manner known per se from the carboxylic acids (Q=OH) on which they are based, for example by reaction with thionyl chloride.

Besides the carbonyl chlorides (Q=Cl), further activated acid derivatives of the type Q(O)C— can also be prepared in a manner known per se directly from the carboxylic acids (Q=OH) on which they are based, such as, for example, the methyl esters (Q=OCH₃) by treating with gaseous HCl in methanol, the imidazolides (Q=1-imidazolyl) by treating with carbonyldiimidazole [cf. Staab, Angew. Chem. Int. Ed. Engl. 1, 351–367 (1962) incorporated references in its entirety], the mixed anhydrides (Q=C₂H₅OC(O)O or TosO) with C₁–COOC₂H₅ or tosyl chloride in the presence of triethylamine in an inert solvent. The activation of the carboxylic acids can also be carried out with dicyclohexylcarbodiimide (DCCI) or with O-[(cyano(ethoxycarbonyl)-methylene)amino]-1,1,3,3-tetramethyluronium tetrafluoroborate ("TOTU") [Weiss and Krommer, Chemiker Zeitung 98, 817 (1974) incorporated herein by reference in its entirety] and other activating reagents customary in peptide chemistry. A number of suitable methods for the preparation of activated carboxylic acid derivatives of the formula II are indicated stating source literature in J. March, Advanced Organic Chemistry, Third Edition (John Wiley & Sons, 1985), p. 350 incorporated herein by reference in its entirety.

The reaction of an activated carboxylic acid derivative of the formula III with the respective guanidine (derivative) is carried out in a manner known per se in a protic or aprotic polar but inert organic solvent. In this context, methanol, isopropanol or THF from 20° C. up to the boiling temperature of these solvents have proven suitable in the reaction of the methyl esters ($Q=OCH_3$) with the respective guanidines. In the case of most reactions of compounds of the formula III with salt-free guanidines, the reaction is advantageously carried out in aprotic inert solvents such as THF, dimethoxyethane, dioxane. However, if a base (such as, for example, NaOH), is used it is also possible to use water as a solvent in the reaction of compounds of the formula III with guanidines. If Q=Cl, the reaction is advantageously carried out with addition of an acid scavenger, e.g. in the form of excess guanidine (derivative) to bind the hydrohalic acid.

Compounds of the formula I in which $R^1$—Y—A— is $R^2$—C(=$NR^2$)—C(O)— or a system comprising a mono- or polycycle of the type

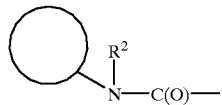

can be obtained analogously.

Compounds of the formula I in which $R^1$—Y—A— is a sulfonyl- or sulfoxylguanidine of the type $R^2R^3N$—C(=$NR^2$)—$NR^2$—$S(O)_n$— (n=1, 2) or a sulfonyl- or sulfoxylaminoguanidine of the type $R^2R^3N$—C(=$NR^2$)—$NR^2$—$NR^2$—$S(O)_n$— (n=1, 2) or

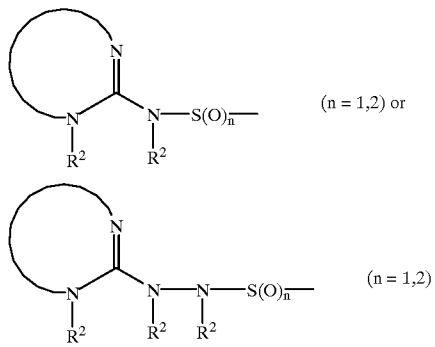

are prepared by processes known from the literature by reaction of $R^2R^3N$—C(=$NR^2$)—$NR^2H$ or $R^2R^3N$—C(=$NR^2$)=13 $NR^2$—$NR^2H$ or

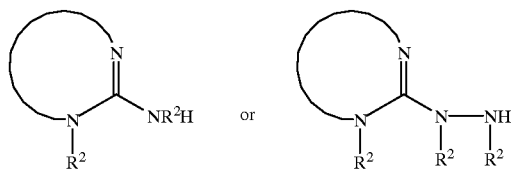

with sulfinic or sulfonic acid derivatives of the formula IV $$Q-S(O)_n-B-D-E-F-G \qquad \text{IV}$$

in which Q, for example, is Cl or $NH_2$, analogously to S. Birtwell et al., J. Chem. Soc. (1946) 491 incorporated herein by references in its entirety, or Houben-Weyl, Methoden der Organischen Chemie [Methods of Organic Chemistry], Vol. E4, Georg Thieme Verlag, Stuttgart 1983; p. 620 et seq.

Compounds of the formula I in which $R^1$—Y—A is $R^2$—C(=$NR^2$)—$NR^2$—$S(O)_n$— (n=1, 2) or $R^2$—C(=$NR^2$)—$NR^2$—$NR^2$—$S(O)_n$— (n=1, 2) or a system comprising a mono- or polycycle of the type

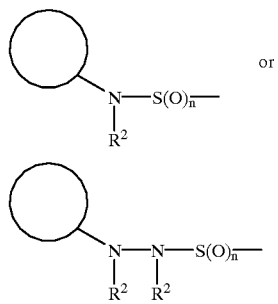

(n=1, 2) can be obtained analogously.

Compounds of the formula I in which Y has the meaning indicated, A is —$NR^2$—C(O)—$NR^2$—, —$NR^2$—C(O)O—, —$NR^2$—C(O)S— and $R^1$ is $R^2R^3N$—C(=$NR^2$)—, $R^2$—C($NR^2$)— or a 4–10-membered mono- or polycyclic, aromatic or nonaromatic ring system which is specified as described above and can be substituted as described there, are prepared, for example, by reacting a compound of the formula V $$Q-B-D-E-F-G \qquad \text{V}$$

in which Q is $HNR^2$—, HO— or HS—, with a suitable carbonic acid derivative, preferably phosgene, diphosgene (trichloromethyl chloroformate), triphosgene (bistrichloromethyl carbonate), ethyl chloroformate, i-butyl chloroformate, bis(1-hydroxy-1-H-benzotriazolyl) carbonate or N,N'-carbonyldiimidazole, in a solvent which is inert to the reagents used, preferably DMF, THF or toluene, at a temperature between −20° C. and the boiling point of the solvent, preferably between 0° C. and 60° C., first to give a substituted carbonic acid derivative of the formula VI

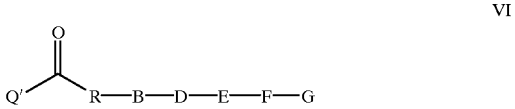

in which R is —$NR^2$—, —O— or —S— and Q', depending on the carbonic acid derivative used, is chlorine, ethoxy, isobutoxy, benzotriazol-1-oxy or 1-imidazolyl.

The reaction of these derivatives—in the case where Y is a direct bond—with $R^2R^3N$—$C(=NR^2)$—$NR^2H$ or $R^2$—$C(=NR^2)$—$NR^2H$ or, if Y is —$NR^2$—, with $R^2R^3N$—$C(=NR^2)$—$NR^2$—$NR^2H$ or $R^2$—$C(=NR^2)$—$NR^2$—$NR^2H$ or with the systems comprising a mono- or polycycle of the type

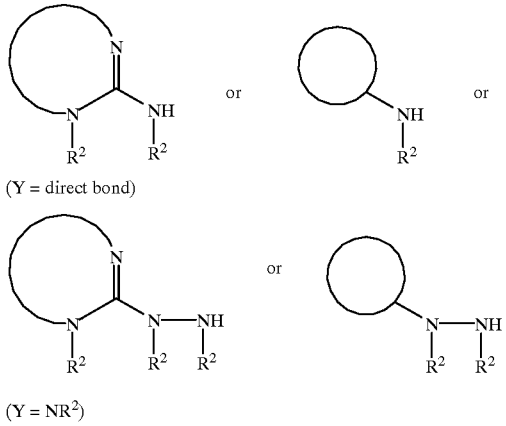

(Y = direct bond)

(Y = $NR^2$)

is carried out as described above in the preparation of acylguanidine (derivatives).

Compounds of the formula I in which F is —$R^2N$—C(O)—$NR^2$— or —$R^2N$—C(S)—$NR^2$— are prepared, for example, by reacting a compound of the formula VII

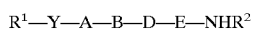
$R^1$—Y—A—B—D—E—$NHR^2$      VII with an isocyanate OCN—G or isothiocyanate SCN—G by processes known from the literature.

Compounds of the formula I in which F is —$C(O)NR^2$—, —$SO_2NR^2$— or —C(O)O— can be prepared, for example, by reaction of

$R^1$—Y—A—B—D—E—C(O)Q or

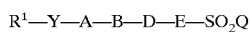
$R^1$—Y—A—B—D—E—$SO_2Q$ (Q is an easily nucleophilically substitutable leaving group, such as, for example, OH, Cl, $OCH_3$ etc.) with $HR^2N$—G or HO—G by processes known from the literature.

Compounds of the formula I in which Y is a bond and $R^1$—A— comprises a mono- or polycycle of the type

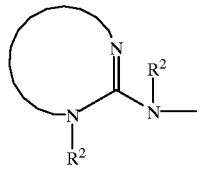

can be prepared, for example, by reacting a compound of the formula VIII

$HR^2N$—B—D—E—F—G      VIII with a mono- or polycycle of the type

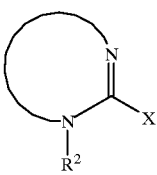

in which X is a nucleophilically substitutable leaving group such as, for example, halogen or SH, $SCH_3$, $SOCH_3$, $SO_2CH_3$ or HN—$NO_2$, by processes known from the literature (see, for example, A. F. Mckay et al., J. Med. Chem. 6 (1963) 587, M. N. Buchman et al., J. Am. Chem. Soc. 71 (1949), 766, F. Jung et al., J. Med. Chem. 34 (1991) 1110 or G. Sorba et al., Eur. J. Med. Chem. 21 (1986), 391) all of which are incorporated by reference in their entireties.

Compounds of the formula I in which Y is a bond and $R^1$—A— comprises a mono- or polycycle of the type

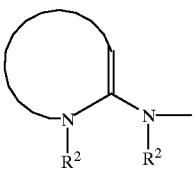

can be prepared, for example, by reacting a compound of the formula VIII with a compound of the type

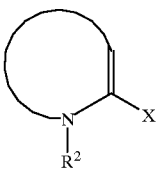

in which X is a leaving group, such as, for example —$SCH_3$, by processes known from the literature (cf., for example, T. Hiroki et al., Synthesis 1984) 703 or M. Purkayastha et al., Indian J. Chem. Sect. B 30 (1991) 646) which is incorporated by reference in its entirety.

Compounds of the formula I in which D is —C≡C— can be prepared, for example, by reacting a compound of the formula IX

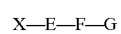
X—E—F—G      IX in which X is I or Br with a compound of the type $R^1$—Y—A—B—C≡—CH in a palladium-catalyzed reaction, such as described, for example, in A. Arcadi et al., Tetrahedron Lett. 1993, 34, 2813 or E. C. Taylor et al. J. Org. Chem. 1990, 55, 3222 both of which are incorporated by reference in their entireties.

Analogously, compounds of the formula I in which F is equal to —C≡C— can be prepared, for example, by linkage of compounds of the formula X

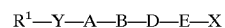
$R^1$—Y—A—B—D—E—X      X in which X is I or Br with a compound of the type HC≡C—G in a palladium-catalyzed reaction.

Preparation processes known from the literature are described, for example, in J. March, Advanced Organic Chemistry, Third Edition (John Wiley & Sons, 1985 which is incorporated by reference).

The compounds of the formula I and their physiologically tolerable salts can be administered to animals, preferably to mammals, and in particular to humans as medicaments by themselves, in mixtures with one another or in the form of pharmaceutical preparations which allow enteral or parenteral administration and which as active constituent contain an efficaceous dose of at least one compound of the formula I or of a salt thereof, in addition to customary pharmaceutically innocuous excipients and additives. The preparations normally contain approximately 0.5 to 90% by weight of the therapeutically active compound.

The medicaments can be administered orally, e.g. in the form of pills, tablets, lacquered tablets, sugar-coated tablets, granules, hard and soft gelatin capsules, solutions, syrups, emulsions, suspensions or aerosol mixtures. Administration can also be carried out rectally, however, e.g. in the form of suppositories, or parenterally, e.g. in the form of injection or infusion solutions, microcapsules or rods, percutaneously, e.g. in the form of ointments or tinctures, or nasally, e.g. in the form of nasal sprays.

The pharmaceutical preparations are prepared in a manner known per se, pharmaceutically inert inorganic or organic excipients being used. For the production of pills, tablets, sugar-coated tablets and hard gelatin capsules, it is possible to use, for example, lactose, maize starch or derivatives thereof, talc, stearic acid or its salts etc. Excipients for soft gelatin capsules and suppositories are, for example, fats, waxes, semisolid and liquid polyols, natural or hardened oils, etc. Suitable excipients for the preparation of solutions and syrups are, for example, water, sucrose, invert sugar, glucose, polyols, etc. Suitable excipients for the production of injection solutions are water, alcohols, glycerol, polyols, vegetable oils, etc. Suitable excipients for microcapsules, implants or rods are copolymers of glycolic acid and lactic acid.

Beside the active compounds and excipients, the pharmaceutical preparations can also contain additives, such as, for example, fillers, extenders, disintegrants, binders, lubricants, wetting agents, stabilizers, emulsifiers, preservatives, sweeteners, colorants, flavorings or aromatizers, thickening agents, diluents, buffer substances, furthermore solvents or solubilizers or agents for achieving a depot effect, and salts for altering the osmotic pressure, coating agents or antioxidants. They can also contain two or more compounds of the formula I or their physiologically tolerable salts; furthermore beside at least one compound of the formula I, also one or more other therapeutically active substances.

The dose can vary within wide limits and is to be suited to the individual conditions in each individual case. In the case of oral administration, the daily dose is in general from 0.01 to 50 mg/kg, preferably 0.1 to 5 mg/kg, in particular 0.3 to 0.5 mg/kg, of bodyweight to achieve efficacious results; in the case of intravenous administration the daily dose is in general approximately 0.01 to 100 mg/kg, preferably 0.05 to 10 mg/kg, of body weight. In particular in the case of the administration of relatively large amounts, the daily dose can be divided into more than one, e.g. 2, 3 or 4, part administrations. In some cases it may be necessary, depending on individual behavior, to deviate upward or downward from the daily dose indicated.

The compounds of the formula I according to the invention inhibit bone resorption by osteoclasts. Bone diseases against which the compounds according to the invention can be employed are especially osteoporosis, hypercalcemia, osteopenia, e.g. caused by metastases, dental disorders, hyperparathyroidism, periarticular erosions in rheumatoid arthritis and Paget's disease.

The compounds of the formula I can furthermore be employed for the alleviation, avoidance or therapy of bone disorders which are caused by a glucocorticoid, steroid or corticosteroid therapy or by a deficiency of sex hormone(s). All these disorders are characterized by bone loss, which is based on the inequilibrium between bone formation and bone destruction.

The compounds of the formula I can furthermore be used as carrier for active compounds in order to transfer the active compounds specifically to the site of action (=drug targeting, see, for example, Targeted Drug Delivery, R. C. Juliano, Handbook of Experimental Pharmacology Vol. 100, Ed. Born, G. V. R. et al., Springer Verlag, which is incorporated by reference in its entirety). The active compounds are those which can be used for the treatment of the abovementioned diseases.

The inhibition of bone resorption by the compounds according to the invention can be determined, for example, with the aid of an osteoclast resorption test ("PIT ASSAY"), for example analogously to WO 95/32710 which is incorporated herein by reference in its entirety. The inhibitory action of the compounds according to the invention against the vitronectin receptor $\alpha_v\beta_3$ can be determined, for example, as described below.

Test method 1:

Inhibition of the binding of human vitronectin ($V_n$) to human vitronectin receptor (VnR) $\alpha_v\beta_3$ (ELISA test)

1. Purification of human vitronectin

Human vitronectin is isolated from human plasma and purified by affinity chromatography according to the method of Yatohyo et al., Cell Structure and Function, 1988, 23, 281–292 which is incorporated by reference.

2. Purification of human vitronectin receptor ($\alpha_v\beta_3$)

Human vitronectin receptor is obtained from human placenta according to the method of Pytela et al., Methods Enzymol. 1987, 144, 475 which is incorporated by reference. Human vitronectin receptor $\alpha_v\beta_3$ can also be obtained from some cell lines (e.g. from 293 cells, a human embryonic kidney cell line), which are cotransfected with DNA sequences for both subunits $\alpha_v$ and $\beta_3$ of the vitronectin receptor. The subunits are extracted with octyl glycoside and then chromatographed on concanavalin A, heparin-Sepharose and S-300.

3. Monoclonal antibodies

Murine monoclonal antibodies, specific for the 3 subunit of the vitronectin receptor, are prepared according to the method of Newman et al., Blood, 1985, 227–232 (which is incorporated by reference), or by a similar process. The rabbit Fab 2 anti-Mouse Fc conjugate to horseradish peroxidase (anti-mouse Fc HRP) was ordered from Pel Freeze (Catalog No. 715 305-1).

4. ELISA Test

Nunc Maxisorp 96-well microtiter plates are coated overnight at 4° C. with a solution of human vitronectin (0.002 mg/ml, 0.05 ml/well) in PBS (phosphate-buffered saline solution). The plates are washed twice with PBS/0.05 % Tween 20 and blocked by incubating (60 min) with bovine serum albumin (BSA, 0.5%, RIA quality or better) in tris HCl (50 mM), NaCl (100 mM), MgCl$_2$ (1 mM), CaCl$_2$ (1 mM), MnCl$_2$ (1 mM), pH 7. Solutions of known inhibitors and of the test substances are prepared in concentrations of $2\times10^{-12}$–$2\times10^6$ mol/l in assay buffer [BSA (0.5%, RIA quality or better) in tris HCl (50 mM), NaCl (100 mM), MgCl$_2$ (1 mM), CaCl$_2$ (1 mM), MnCl$_2$ (1 mM), pH 7]. The blocked plates are emptied, and in each case 0.025 ml of this solution, which contained a defined concentration ($2 \times 10^{-12}$ to $2 \times 10^{-6}$) either of a known inhibitor or of a test substance, is added to each well. 0.025 ml of a solution of the vitronectin receptor in the test buffer (0.03 mg/ml) is pipetted into each well of the plate and the plate is incubated at room temperature for 60–180 min on a shaker. In the meantime, a solution (6 ml/plate) of a murine monoclonal antibody specific for the $\beta_3$ subunit of the vitronectin receptor is prepared in the assay buffer (0.0015 mg/ml). A second rabbit antibody (0.001 ml of stock solution/6 ml of the murine monoclonal anti-$\beta_3$-antibody solution), which is an anti-mouse Fc HRP antibody conjugate, is added to this solution and this mixture of murine anti-$\beta_3$ antibody and rabbit anti-mouse Fc HRP antibody conjugate is incubated for the time of the receptor-inhibitor incubation.

The test plates are washed 4 times with PBS solution which contains 0.05% Tween 20 and 0.05 ml/well in each case of the antibody mixture is pipetted into each well of the plate and incubated for 60–180 min. The plate is washed 4 times with PBS/0.05 % Tween 20 and then developed with 0.05 ml/well of a PBS solution which contains 0.67 mg/ml of o-phenylenediamine and 0.012% $H_2O_2$. Alternatively to this, o-phenylenediamine can be employed in a buffer (pH 5) which contains $Na_3PO_4$ (50 mM) and citric acid (0.22 mM). The color development is stopped with 1 N $H_2SO_4$ (0.05 ml/well). The absorption of each well is measured at 492–405 nm and the data are analyzed according to standard methods.

Test method 2:

Inhibition of the binding of kistrin to human vitronectin receptor (VnR) $\alpha_v\beta_3$ (ELISA Test)

(Test method 2 is abbreviated as Kistrin/VnR in the listing of the test results)

1. Purification of kistrin

Kistrin is purified according to the methods of Dennis et al., as described in Proc. Natl. Acad. Sci. USA 1989, 87, 2471–2475 and PROTEINS: Structure, Function and Genetics 1993, 15, 312–321 both of which are incorporated by reference.

2. Purification of human vitronectin receptor ($\alpha_v\beta_3$)

see Test method 1.

3. Monoclonal antibodies see Test method 1.

4. ELISA Test

The ability of substances to inhibit the binding of kistrin to the vitronectin receptor can be determined using an ELISA test. For this purpose, Nunc 96-well microtiter plates are coated with a solution of kistrin 0.002 mg/ml according to the method of Dennis et al., as described in PROTEINS: Structure, Function and Genetics 1993, 15, 312–321. The further experimental procedure of the ELISA Test is carried out as described in Test method 1, item 4.

Test method 3:

Inhibition of the binding of 293 cells transfected with $\alpha_v\beta_3$ to human vitronectin Cell test 293 cells, a human embryonic kidney cell line, which are cotransfected with DNA sequences for the $\alpha_v$ and $\beta3$ subunits of the vitronectin receptor are selected according to the FACS method with a view to a high expression rate (>500,000 $\alpha_v\beta_3$ receptors/cell). The selected cells are cultured and sorted again by means of FACS to obtain a stable cell line (15 D) with expression rates of >1,000,000 copies of $\alpha_v\beta_3$ per cell.

A Linbro 96-well tissue culture plate with a flat bottom is coated overnight at 4° C. with human vitronectin (0.01 mg/ml, 0.05 ml/well) in phosphate-buffered saline solution (PBS) and then blocked with 0.5% strength BSA. Solutions of the test substances from $10^{-10}$–$2 \times 10^{-3}$ mol/l in glucose-containing DMEM medium are prepared and in each case 0.05 ml/well of the solution is added to the plate. The cells which express high levels of $\alpha_v\beta_3$ (e.g. 15 D) are suspended in glucose-containing DMEM medium and the suspension is adjusted to a content of 25,000 cells/0.05 ml of medium. 0.05 ml of this cell suspension is added to each well and the plate was incubated at 37° C. for 90 min. The plate is washed 3× with warm PBS to remove unbound cells. The bound cells are lysed in citrate buffer (25 mmol, pH 5.0), which contains 0.25% Triton X-100. The hexose amidase substrate p-nitrophenyl-N-acetyl-$\beta$-D-glucosaminide is then added and the plate is incubated at 37° C. for 90 min. The reaction is stopped with a glycine (50 mmol)/EDTA (5 mmol) buffer (pH 10.4) and the absorption of each well is measured at 405–650 nm. The data are evaluated using standard methods.

The following test results were obtained:

Kistrin/VnR $IC_{50}$ ($\mu$M)

Compound of example 1 0.03

EXAMPLES

Reference will now be made to the following non-limiting examples. The products were identified by means of mass spectra and/or NMR spectra.

Example 1

4-[2-(N-(Imidazolin-2-yl)hydrazonoethyloxy)]benzoyl-(2S)-2-benzyloxy-carbonylamino-$\beta$-alanine hydrobromide The synthesis was carried out according to the following reaction sequence:

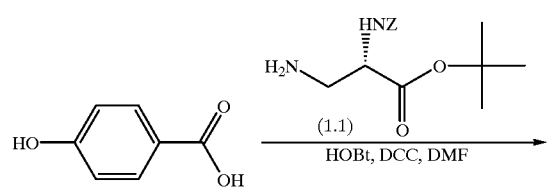

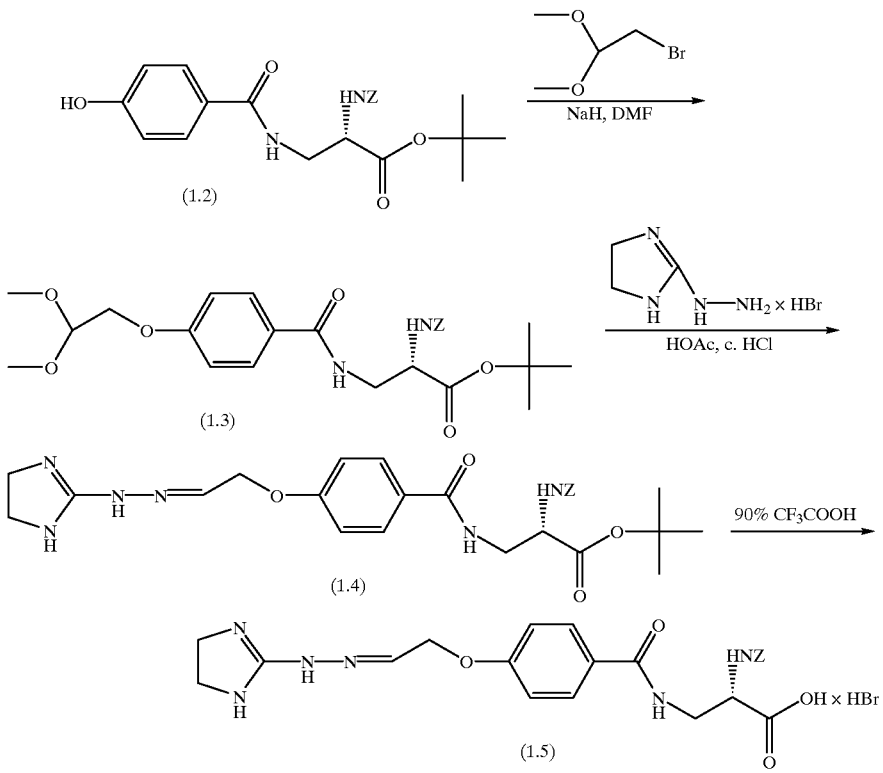

1a) tert-Butyl (2S)-3-amino-2-benzyloxycarbonylaminopropionate (1.1)

10 g (42 mmol) of (2S)-3-amino-2-benzyloxycarbonylaminopropionic acid were shaken in an autoclave at 20 atm. $N_2$ pressure for 3 days in a mixture of 100 ml of dioxane, 100 ml of isobutylene and 8 ml of conc. $H_2SO_4$. Excess isobutylene was blown out and 150 ml of diethyl ether and 150 ml of saturated $NaHCO_3$ solution were added to the remaining solution. The phases were separated and the aqueous phase was extracted twice using 100 ml of diethyl ether each time. The combined organic phases were washed with 2×100 ml of $H_2O$ and dried over $Na_2SO_4$. After removing the solvent in vacuo, (1.1) were obtained as a pale yellow oil.

1b) 4-Hydroxybenzoyl-(2S)-2-benzyloxycarbonylamino-β-alanine tert-butyl ester (1.2)

1.41 g (10.2 mmol) of 4-hydroxybenzoic acid and 3 g (10.2 mmol) of (1.1) were suspended in 25 ml of DMF. 1.38 g (10.2 mmol) of 1-hydroxy-benzotriazole (HOBt) and, at 0° C., dicyclohexylcarbodiimide (DCCI) were added. The mixture was stirred at 0° C. for 1 h and allowed to stand at room temperature overnight. After filtration, the solvent was removed in vacuo and the residue was chromatographed on silica gel by means of MPLC using heptane/ethyl acetate (1/1). (1.2) was obtained as a colorless solid; melting point 69° C.

1c) 4(2,2-Dimethoxyethyloxy)-benzoyl-(2S)-2-benzyloxycarbonylamino-β-alanine tert-butyl ester (1.3)

1.8 g (4.34 mmol) of (1.2) were added to a suspension of 176 mg of a 55% strength sodium hydride suspension in oil (4.07 mmol of sodium hydride) in 10 ml of abs. DMF and the mixture was stirred until the evolution of hydrogen was complete (about 30 min). 620 mg (3.7 mmol) of bromoacetaldehyde dimethyl acetal were then added and the mixture was heated at 50° C. for 8 h and at 70° C. for 2 h. After fresh addition of 18 mg of the sodium hydride suspension in oil (0.41 mmol of sodium hydride), the mixture was heated at 70° C. for a further 4 h. After standing overnight, the reaction mixture was concentrated in a rotary evaporator and the residue was partitioned between $H_2O$ and $CH_2Cl_2$. The organic phase was separated off and dried over $MgSO_4$, and the solvent was removed in vacuo. The residue was chromatographed on silica gel by means of MPLC using heptane/ethyl acetate. (1.3) was obtained as a colorless solid; melting point 115° C.

1d) 4-[2-(N-(Imidazolin-2-yl)hydrazonoethyloxy)]benzoyl-(2S)-2-benzyloxycarbonylamino-β-alanine tert-butyl ester hydrobromide (1.4)

150 mg (0.3 mmol) of (1.3) and 54 mg (0.3 mmol) of 2-hydrazino-2-imida-zoline hydrobromide were dissolved in 3 ml of conc. acetic acid and treated with one drop of conc. hydrochloric acid. After 5 h at room temperature, the reaction mixture was poured into diethyl ether. The precipitate was centrifuged off, triturated with diethyl ether and centrifuged off again and, after drying in vacuo, directly reacted to give (1.5) (see 1e).

1e) 4-[2-(N-(Imidazolin-2-yl)hydrazonoethyloxy)]benzoyl-(2S)-2-benzyloxycarbonylamino-1-alanine hydrobromide (1.5)

The crude product (1.4) from 1d) was treated with 90% strength trifluoroacetic acid. After 1 h at room temperature, the trifluoroacetic acid was removed in vacuo and the residue was crystallized using $H_2O$/n-butanol/HOAc (43/4.3/3.5). (1.5) was obtained as a colorless solid; melting point 219° C. (decomposition).

Other embodiments of the invention will be apparent to those skilled in the art from consideration of the specification and practice of the invention disclosed herein. It is intended that the specification be considered as exemplary only, with the true scope and spirit of the invention being indicated by the following claims.

Priority application German 19629817.2 filed Jul. 24, 1996, including the title, specification, claims and abstract, is hereby incorporated by reference.

What is claimed is:

1. A compound of formula (1),

$$R^1—Y—A—B—D—E—F—G \qquad (1),$$

in which:

A is a direct bond, $(C_1–C_8)$-alkanediyl, $—NR^2—N=CR^2—$, $—NR^2—C(O)—NR^2—$, $—NR^2—C(O)O—$, $—NR^2—C(O)S—$, $—NR^2—C(S)—NR^2—$, $—NR^2—C(S)—O—$, $—NR^2—C(S)—S—$, $—NR^2—S(O)_n—NR^2$, $—NR^2—S(O)_n—O—$, $—NR^2—S(O)_n—$, $(C_3–C_{12})$-cycloalkanediyl, $—C≡C—$, $—NR^2—C(O)—$, $—C(O)—NR^2—$, $—(C_5–C_{14})$-arylene-C(O)—NR^2—$, $—O—$, $—S(O)_n—$, $—(C_5–C_{14})$-arylene-, $—CO—$, $—(C_5–C_{14})$-arylene-CO—, $NR^2—$, $—SO_2—NR^2—$, $—CO_2—$, $—N=CR^2—$, $—R^2C=N—$, $—CR^2=CR^3—$, $—(C_5–C_{14})$-arylene-S(O)_n—$, wherein each case is unsubstituted or mono- or disubstituted by $(C_1–C_8)$-alkanediyl;

B is a direct bond, $(C_1–C_8)$-alkanediyl, $—CR^2=CR^3—$ or $—C≡C—$, wherein each case is unsubstituted or mono- or disubstituted by $(C_1–C_8)$-alkanediyl, or a divalent radical of a 5- or 6-membered saturated or unsaturated ring, which contains from 0 to 2 nitrogen atom and is unsubstituted or mono-or disubstituted by $(C_1–C_6)$-alkyl or doubly bonded oxygen or sulfur;

D is a direct bond, $(C_1–C_8)$-alkanediyl, or $—O—$, $—NR^2—$, $—CO—NR^2—$, $—NR^2—CO—$, $—NR^2—C(O)—NR^2—$, $—NR^2—C(S)—NR^2—$, $—OC(O)—$, $—C(O)O—$, $—CO—$, $—CS—$, $—S(O)—$, $—S(O)_2—$, $S(O)_2—NR^2—$, $—NR^2—S(O)—$, $—NR^2—S(O)_2—$, $—S—$, $—CR^2=CR^3—$, $—C≡C—$, $—NR^2—N=CR^2—$, $—N=CR^2—$, $—R^2C=N—$ or $—CH(OH)—$, wherein each case is unsubstituted or mono- or disubstituted by $(C_1–C_8)$-alkanediyl;

E is a 6-membered aromatic ring system, which contains from 0 to 4 nitrogen atoms and is unsubstituted or substituted by 1–4 identical or different radicals selected from the group consisting of $R^2$, $R^3$, fluorine, Cl, Br, I, $NO_2$ and OH;

F is selected from the group consisting of the same constituents as defined for D and is the same or different than D;

G is

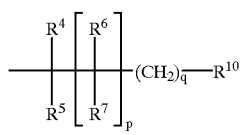

Y is a direct bond or $—NR^2—$;

$R^1$ is $—C(=NR^2)—NR^2—$, $R^2R^3N—C(=NR^2)—$, $R^2R^3N—C(=NR^2)—NR^2—$, or a 4–10-membered mono- or polycyclic aromatic or nonaromatic ring system, substituted with from 0 to 4 heteroatoms selected from the group consisting of N, O and S and is unsubstituted or monosubstituted or polysubstituted by substituents selected from the group consisting of $R^{12}$, $R^{13}$, $R^{14}$ and $R^{15}$;

$R^2$, $R^3$ independently of one another are H, $(C_1–C_{10})$-alkyl, which is unsubstituted or mono- or polysubstituted by fluorine, $(C_3–C_{12})$-cyclo-alkyl, $(C_3–C_{12})$-cycloalkyl-$(C_1–C_8)$-alkanediyl, $(C_5–C_{14})$-aryl, $(C_5–C_{14})$-aryl-$(C_1–C_8)$-alkanediyl, $H_2N$, $(R^8O)R^8NR^9$, $R^8OR^9$, $R^8OC(O)R^9$, $R^8—(C_1–C_{14})$-arylene-$R^9$, $R^8R^8NR^9$, $HO—(C_1–C_8)$-alkanediyl-$NR^8R^9$, $R^8R^8NC(O)R^9$, $R^8C(O)NR^8R^9$, $R^8C(O)R^9$, $R^8R^8N—C(=NR^8)—$, $R^8R^8N—C(=NR^8)—NR^8—$ or $(C_1–C18)$-alkylcarbonyloxy-$(C_1–C_6)$-alkanediyloxycarbonyl;

$R^4$, $R^5$, $R^6$, $R^7$ independently of one another are H, fluorine, OH, $(C_1–C_8)$-alkyl, $(C_3–C_{12})$-cycloalkyl, $(C_3–C_{12})$-cycloalkyl-$(C_1–C_8)$-alkanediyl, or $R^8OR^9$, $R^8SR^9$, $R^8CO_2R^9$, $R^8OC(O)R^9$, $R^8—(C_5–C_{14})$-arylene-$R^9$, $R^8N(R^2)R^9$, $R^8R^8NR^9$, $R^8N(R^2)C(O)OR^9$, $R^8S(O)_nN(R^2)R^9$, $R^8OC(O)N(R^2)R^9$, $R^8C(O)N(R^2)R^9$, $R^8N(R^2)C(O)N(R^2)R^9$, $R^8N(R^2)S(O)_nN(R^2)R^9$, $R^8S(O)_nR^9$, $R^8SC(O)N(R^2)R^9$, $R^8C(O)R^9$, $R^8N(^2)C(O)R^9$, or $R^8N(R^2)S(O)_nR^9$;

$R^8$ is H, $(C_1–C_8)$-alkyl, $(C_3–C_{12})$-cycloalkyl, $(C_3–C_{12})$-cycloalkyl-$(C_1–C_8)$-alkanediyl, $(C_5–C_{14})$-aryl, or $(C_5–C_{14})$-aryl-$(C_1–C_8)$-alkanediyl, wherein alkyl or cycloalkyl or alkanediyl is unsubstituted or mono- or polysubstituted by fluorine;

$R^9$ is a direct bond or $(C,–C_8)$-alkanediyl;

$R^{10}$ is $C(O)R^{11}$, $C(S)R^{11}$, $S(O)_nR^{11}$, $P(O)(R^{11})_n$ or a four- to eight-membered, saturated or unsaturated heterocycle which contains 1, 2, 3 or 4 heteroatoms selected from the group consisting of: N, O and S;

$R^{11}$ is OH, $(C_1–C_8)$-alkoxy, $(C_5–C_{14})$-aryl-$(C_1–C_8)$-alkanediyloxy, $(C_5–C_{14})$aryloxy, $(C_1–C_8)$-alkylcarbonyloxy-$(C_1–C_4)$-alkanediyloxy, $(C_5–C_{14})$-aryl-$(C_1–C_8)$-alkanediylcarbonyloxy-$(C_1–C_6)$-alkanediyloxy, $NH_2$, mono- or di-$(C_1–C_8$-alkyl)-amino, $(C_5–C_{14})$-aryl-$(C_1–C_8)$-alkanediylamino, $(C_1–C_8)$-dialkylaminocarbonylmethylenoxy, $(C_5–C_{14})$-aryl-$(C_1–C_8)$-dialkylaminocarbonylmethylenoxy or $(C_5–C_{14})$-arylamino or a radical of an L- or D-amino acid;

$R^{12}$, $R^{13}$, $R^{14}$, $R^{15}$ independently of one another are H, $(C_1–C_{10})$-alkyl, wherein each case is unsubstituted or mono- or polysubstituted by fluorine, $(C_3–C_{12})$-cycloalkyl, $(C_3—C_{12})$-cycloalkyl-$(C_1–C_8)$-alkanediyl, $(C_5–C_{14})$-aryl, $(C_5–C_{14})$-aryl-$(C_1–C_8)$-alkanediyl, $H_2N$, $(R^8O)R^8NR^9$, $R^8OR^9$, $R^8OC(O)R^9$, $R^8R^8NR^9$, $R^8—(C_5–C_{14})$-arylene-$R^9$, $HO—(C_1–C_8)$-alkanediyl-$N(R^2)R^9$, $R^8N(R^2)C(O)R^9$, $R^8C(O)N(R^2)R^9$, $R^8C(O)R^9$, $R^2R^3N—C(=NR^2)—NR^2—$, $R^2R^3N—C(=NR^2)—$, $=O$, or $=S$;

n is 1 or 2;

p, q independently of one another are 0 or 1;

in all their stereoisomeric forms or mixtures thereof in any ratio; or their physiologically tolerable salts;

wherein at least one of the groups A, D or F is $—NR^2—N=CR^2—$, $—N=CR^2—$ or $—R^2C=N—$.

2. A compound of the formula (I) as claimed in claim 1, in which:

A is a direct bond, $(C_1–C_6)$-alkanediyl, $—NR^2—N=CR^2—$, $—NR^2—C(O)—NR^2—$, $NR^2—C(O)O—$, $—NR^2—C(O)S—$, $—NR^2—C(S)—NR^2—$, $—NR^2—C(S)—O—$, $—NR^2—C(S)—S—$, $—NR^2—S(O)$, $—NR^2—$, $—NR^2—S(O)_n—O—$, $—NR^2—S(O)_n—$, ($C_3$–$C_8$)-cycloalkanediyl, —C≡C—, —$NR^2$—C(O)—, —C(O)—$NR^2$—, —($C_5$–$C_{12}$)-arylene-C(O)—$NR^2$—, —O—, —S(O)$_n$—, ($C_5$–$C_{12}$)-arylene-, —CO—, —($C_5$–$C_{12}$-arylene-CO—, —$NR^2$—, —$SO^2$—$NR^2$—, —$CO2$—, —N=$CR^2$—, —$R^2$C=N—, —$CR^2$=$CR^3$—, or —($C_5$–$C_{12}$)-arylene-S(O)$_n$—, wherein each case is unsubstituted or mono- or disubstituted by ($C_1$–$C_8$)-alkanediyl;

B is a direct bond, ($C_1$–$C_8$)-alkanediyl, —$CR^2$=$CR^3$— or —C≡C—, wherein each case is either unsubstituted or mono- or disubstituted by ($C_1$–$C_8$)-alkanediyl;

D is a direct bond, ($C_1$–$C_8$)-alkanediyl, —O—, —$NR^2$—, —CO—$NR^2$—, —$NR^2$—CO—, —$NR^2$—C(O)—$NR^2$—, —$NR^2$—C(S)—$NR^2$—, —OC(O)—, —C(O)O—, —CO—, —CS—, —S(O)—, —S(O)$_2$—, S(O)$_2$$NR^2$—, —$NR^2$—S(O)—, —$NR^2$—S(O)$_2$—, —S—, —$CR^2$=$CR^3$—, —C≡C—, —$NR^2$—N=$CR^2$—, —N=$CR^2$— or —$R^2$C=N—, wherein each case is unsubstituted or mono- or disubstituted by ($C_1$–$C_6$)-alkanediyl;

E is a 6-membered aromatic ring system, which contains from 0 to 2 nitrogen atoms and is unsubstituted or substituted by 1–3 identical or different radicals selected from the group consisting of $R^2$, $R^3$, fluorine, Cl and OH;

F is selected from the group consisting of the same constituents as defined for D and is the same or different than D;

G is

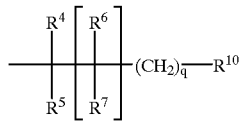

Y is a direct bond or —$NR^2$—;

$R^1$ is $R^2$—C(=$NR^2$)—$NR^3$—, $R^2R^3$N—C(=$NR^2$)—, $R^2R^3$N—C(=$NR^2$)—$NR^2$—, or a 4–10-membered mono- or polycyclic aromatic or nonaromatic ring system substituted with from 0 to 4 heteroatoms selected from the group consisting of N, O and S; and is unsubstituted or monosubstituted or polysubstituted by substituents selected from the group consisting of $R^{12}$, $R^{13}$, $R^{14}$ and $R^{15}$;

$R^2$, $R^3$ independently of one another are H, ($C_1$—$C_8$)-alkyl, which is unsubstituted or mono- or polysubstituted by fluorine, ($C_3$–$C_8$)-cycloalkyl, ($C_3$–$C_8$)-cycloalkyl-($C_1$–$C_6$)alkanediyl, ($C_5$–$C_{12}$)-aryl, ($C_5$–$C_{12}$)-aryl-($C_1$–$C_6$)-alkanediyl, $H_2$N, ($R^8$O)$R^8$$NR^9$, $R^8$O$R^9$, $R^8$OC(O)$R^9$, $R^8$—($C_5$–$C_{12}$)-arylene-$R^9$, $R^8R^8$N$R^9$, HO—($C_1$–$C_8$)-alkanediyl—N$R^8R^9$, $R^8R^8$NC(O)$R^9$, $R^8$(O)N$R^8R^9$, $R^8$C(O)$R^9$, $R^8R^8$N—C(=$R^8$N—C(=N$R^8$)—N$R^8$— or ($C_1$–$C_{10}$)-alkylcarbonyloxy-($C_1$–$C_4$)-alkanediyloxycarbonyl $R^4$, $R^5$, $R^6$, $R^7$ independently of one another are H, fluorine, OH, ($C_1$–$C_8$)-alkyl, ($C_3$—$C_8$)-cycloalkyl, ($C_3$–$C_8$)-cycloalkyl-($C_1$–$C_8$)-alkanediyl, or $R^8$O$R^9$, $R^8$S$R^9$, $R^8$CO$_2R^9$, $R^8$C(O)$R^9$, $R^8$—($C_5$–$C_{12}$)-arylene-$R^9$, $R^8$N($R^2$)$R^5$, $R^8R^8$N$R^9$, $R^8$N($R^2$)C(O)O$R^9$, $R^8$S(O)$_n$N($R^2$)$R^9$, $R^8$OC(OC)N($R^2$)$R^9$, $R^8$C(O)N($R^2$)$R^9$, $R^8$N($R^2$)C(O)N($R^2$)$R^9$, $R^8$N($R^2$)S(O)$_n$($R^2$)$R^9$, $R^8$S(O)$R^9$, $R^8$SC(O)N($R^2$)$R^9$, $R^8$C(O)$R^9$, $R^8$N($R^2$)C(O)$R^9$, or $R^8$N($R^2$)S(O)$_n$$R^9$;

$R^8$ is H, ($C_1$–$C_6$)-alkyl, ($C_3$–$C_8$)-cycloalkyl, ($C_3$–$C_8$)-cycloalkyl-($C_1$–$C_6$)-alkanediyl, ($C_5$–$C_{12}$)-aryl, or ($C_5$–$C_{12}$)-aryl-($C_1$–$C_6$)-alkanediyl, wherein any alkyl or any cycloalkyl or any alkanediyl is either unsubstituted or mono- or polysubstituted by fluorine;

$R^9$ is a direct bond or ($C_1$–$C_6$)-alkanediyl;

$R^{10}$ is C(O)$R^1$, C(S)$R^{11}$, S(O)$R^{11}$P(O)($R^{11}$)$_n$ or a four to eight-membered, saturated or unsaturated heterocycle which contains 1, 2, 3 or 4 heteroatoms selected from the group consisting of N, O and S;

$R^{11}$ is OH, ($C_1$–$C_6$)-alkoxy, ($C_5$–$C_{12}$)-aryl-($C_1$–$C_6$)-alkanediyloxy, ($C_5$–$C_{12}$)-aryloxy, ($C_1$–$C_6$)-alkylcarbonyloxy-($C_1$–$C_4$)alkanediyloxy, ($C_5$–$C_{12}$)-aryl-($C_1$–$C_6$)-alkanediylcarbonyloxy-($C_1$–$C_6$)-alkanediyloxy, $NH_2$, mono- or di-($C_1$–$C_6$-alkyl)-amino, ($C_5$–$C_{12}$)-aryl-($C_1$–$C_6$)-alkanediylamino, or ($C_1$–$C_6$)-dialkylaminocarbonylmethylenoxy;

$R^{12}$, $R^{13}$, $R^{14}$, $R^{15}$ independently of one another are H, ($C_1$–$C_8$)-alkyl, wherein each case is either unsubstituted or mono- or polysubstituted by fluorine, ($C_3$–$C_8$)-cycloalkyl, ($C_3$–$C_8$)cycloalkyl-($C_1$–$C_6$)-alkanediyl, ($C_5$–$C_{12}$)-aryl, ($C_5$–$C_{12}$)-aryl-($C_1$–$C_6$)-alkanediyl, $H_2$N, ($R^8$O)$R^8$N$R^9$, $R^8$OR9, $R^8$OC(O)$R^9$, $R^8$—($C_5$–$C_{12}$)-arylene-$R^9$, $R^8R^8$N$R^9$, HO—($C_1$–$C_8$)-alkanediyl-N($R^2$)$R^9$, $R^8$N($R^2$)C(O)$R^9$, $R^8$C(O)N($R^2$)$R^9$, $R^8$C(O)$R^9$, $R^2R^3$N—C(=N$R^2$)—, $R^2R^3$N—C(=N$R^3$)—N$R^2$—,=O, or =S;

n is 1 or 2;

p, q independently of one another are 0 or 1;

in all their stereoisomeric forms or mixtures thereof in any ratio; or their physiologically tolerable salts.

3. A compound of the formula (I) as claimed in claim 1, in which:

A is a direct bond, ($C_1$–$C_6$)-alkanediyl, —$NR^2$—N=$CR^2$—, —$NR^2$—C(O)—, —C(O)—$NR^2$—, —($C_5$–$C_{10}$)-arylene-, —CO—, —$NR^2$—, —$CO_2$—, —N=$CR^2$—, —$R^2$C=N , or —$CR^2$=$CR^3$—, wherein each case is unsubstituted or mono- or disubstituted by (C—$C_6$)-alkanediyl;

B is a direct bond, ($C_1$–$C_6$)-alkanediyl, or —$CR^2$=$CR^3$—, wherein each case is unsubstituted or mono- or disubstituted by ($C_1$–$C_6$)-alkanediyl;

D is a direct bond, ($C_1$–$C_6$)-alkanediyl, —O—, —$NR^2$—, —$NR^2$—CO—, —C(O)—$NR^2$—, —$NR^2$—C(O)—$NR^2$—, —$NR^2$—C(S)—$NR^2$—, —OC(O)—, —C(O)—, —$CR^2$=$CR^3$—, —$NR^2$—S(O)$_2$—, —N=$CR^2$— or —$R^2$C=N—, wherein each case is unsubstituted or mono- or disubstituted by ($C_1$–$C_6$)-alkanediyl;

E is phenylene or pyridinediyl; wherein each is either unsubstituted or substituted by 1–3 identical or different radicals selected from the group consisting of $R^2$ and $R^3$;

F is a direct bond, ($C_1$–$C_6$)-alkanediyl, —O—, —CO—$NR^2$, —$NR^2$—CO—, —$NR^2$—C(O)—$NR^2$—, —OC(O)—, —C(O)O—, —CO—, —S(O)$_2$—, —S(O)$_2$—$NR^2$—, —$NR^2$—S(O)$_2$—, —$CR^2$=$CR^3$—, or —C≡C—, wherein each case is unsubstituted or mono- or disubstituted by ($C_1$–$C_6$)-alkanediyl;

G is

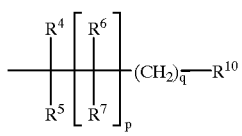

Y is a direct bond or —NH—;

R¹ is R²C(=NR²)—NR²—, R²R³N—C(=NR²)—,

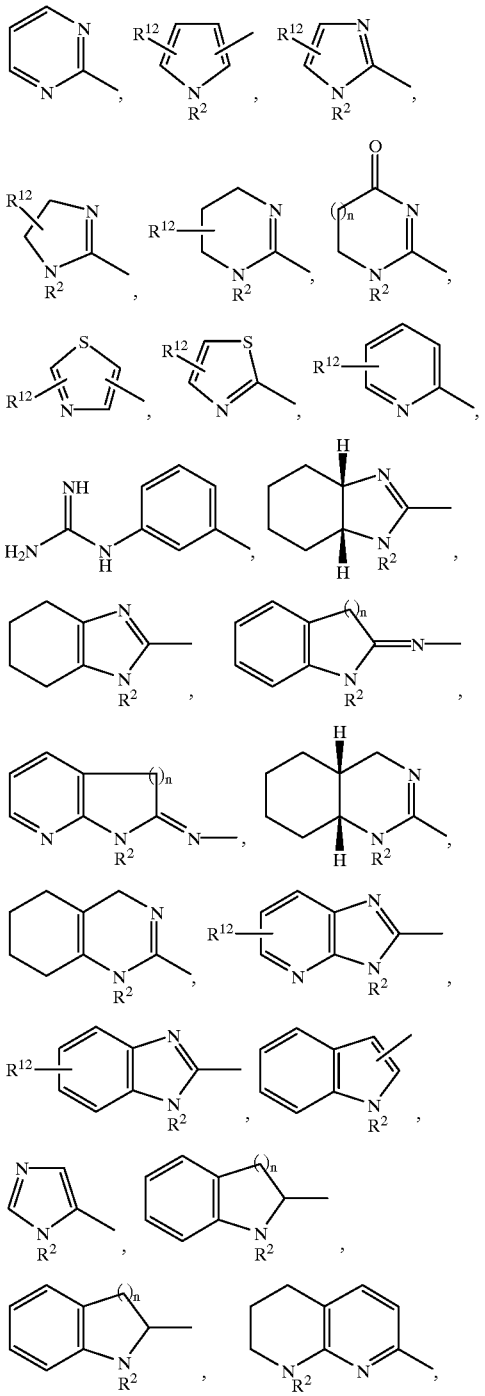

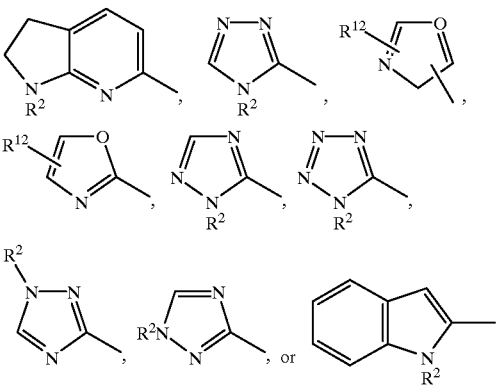

$R^2$, $R^3$ independently of one another are H, $(C_1-C_6)$-alkyl, wherein each is unsubstituted or mono- or polysubstituted, by fluorine, $(C_3-C_6)$-cycloalkyl, $(C_3-C_6)$-cycloalkyl-$(C_1-C_4)$-alkanediyl, $(C_5-C_{10})$-aryl, $(C_5-C_{10})$-aryl-$(C,-C_4)$-alkanediyl, $H_2N$, $R^8OR^9$, $R^8R^8NR^9$, $R^8NHC(O)R^9$, $H_2N$—C(=NH)—, or $H_2N$—C(=NH)—NH—;

$R^4$, $R^5$, $R^6$, $R^7$ independently of one another are H, fluorine, OH, $(C_1-C_6)$-alkyl, $(C_3-C_6)$-cycloalkyl, $(C_3-C_6)$-cycloalkyl-$(C_1-C_6)$-alkanediyl, or $R^8OR^9$, $R^8CO_2R^9$, $R^8OC(O)R^9$, $R^8$—$(C_5-C_{10})$-arylene-$R^9$, $R^8NHR^9$, $R^8R^8NR^9$, $R^8NHC(O)OR^9$, $R^8S(O)_n$—$NHR^9$, $R^8OC(O)NHR^9$, $R^8C(O)NHR^9$, $R^8C(O)R^9$, $R^8NHC(O)NHR^9$, $R^8NHS(O)_n$—$NHR^9$, $R^8NHC(O)R^9$, or $R^8NHS(O)_nR^9$ $R^8$ is H, $(C_1-C_6)$-alkyl, $(C_3-C_6)$-cycloalkyl, $(C_3-C_6)$-cycloalkyl-$(C_1-C_4)$-alkanediyl, $(C_5-C_{10})$-aryl, or $(C_5-C_{10})$-aryl-$(C_1-C_4)$-alkanediyl, wherein alkyl or cycloalkyl or alkanediyl is unsubstituted or substituted by 1–6 fluorine atoms;

$R^9$ is a direct bond or $(C_1-C_6)$-alkanediyl;

$R^{10}$ is $C(O)R^{11}$;

$R^{11}$ is OH, $(C_1-C_6)$-alkoxy, $(C_5-C_{10})$-aryl-$(C_1-C_6)$-alkanediyloxy, $(C_5-C_{10})$-aryloxy, $(C_1-C_6)$-alkylcarbonyloxy-$(C_1-C_4)$-alkanediyloxy, $(C_5-C_{10})$-aryl-$(C_1-C_4)$-alkanediylcarbonyloxy$(C_1-C_4)$-alkanediyloxy, $NH_2$, or mono- or di-$(C_1-C_6$-alkyl)-amino;

$R^{12}$ is H, $(C_1-C_6)$-alkyl which is unsubstituted or mono- or polysubstituted by fluorine, $(C_3-C_6)$-cycloalkyl, $(C_3-C_6)$-cycloalkyl-$(C_1-C_4)$-alkanediyl, $(C_5-C_{10})$-aryl, $(C_5-C_{10})$-aryl-$(C_1-C_4)$-alkanediyl, $H_2N$, $R^8OR^9$, $R^8OC(O)R^9$, $R^8$—$(C_5-C_{10})$-arylene-$R^9$, $R^8R^8NR^9$, $R^8NHC(O)R^9$, $R^8C(O)NHR^9$, $H_2N$—C(=NH)—, $H_2N$—C(=NH)—NH—, =O;

n is 1 or 2;

p, q independently of one another are 0 or 1;

in all their stereoisomeric forms or mixtures thereof in any ratio; or their physiologically tolerable salts.

4. A compound of the formula (I) as claimed in claim 1, in which:

A is a direct bond, —NR²—N=CR²— or —N=CR²—;

B is a direct bond or $(C_1-C_6)$-alkanediyl;

D is a direct bond, $(C_1-C_4)$-alkanediyl or —O—, —NR²—, —NR²—CO—, —C(O)—NR²—, —NR²—C(O)—NR²—, —N=CR²— or —R²C=N—, wherein each case is unsubstituted mono- or disubstituted by $(C_1-C_6)$-alkanediyl;

E is phenylene or pyridinediyl either unsubstituted or substituted by 1 or 2 radicals selected from the group consisting of $R^2$ and $R^3$;

F is a direct bond, $(C_1-C_6)$-alkanediyl, —O—, —CO—NR$^2$—, —NR$^2$—CO—, NR$^2$—C(O)—NR$^2$—, —CR$^2$=CR$^3$— or —C C—, wherein each case is unsubstituted or mono- or disubstituted by $(C_1-C_4)$-alkanediyl;

G is

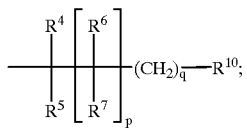

Y is a direct bond or —NH—;

$R^1$ is $R^2R^3N$—C(=NR$^2$)—,

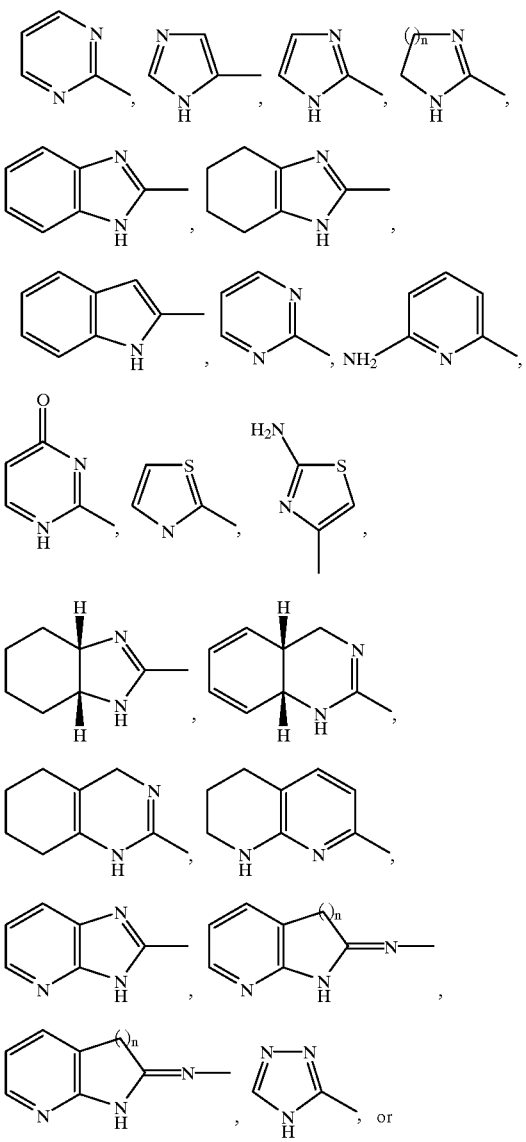

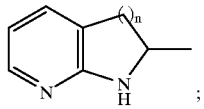

$R^2$, $R^3$ independently of one another are H, $(C_1-C_6)$-alkyl, trifluoromethyl, pentafluoroethyl, $(C_5-C_6)$-cycloalkyl, $(C_5-C_6)$-cycloalkyl-$(C_1-C_2)$ alkanediyl, phenyl, benzyl, H$_2$N, R$^8$OR$^9$, R$^8$R$^8$R$^9$, R$^8$NHC(O)R$^9$, H$_2$N—C(=NH)—, or H$_2$N—C(=NH)—NH—;

$R^4$, $R^5$, $R^6$, $R^7$ independently of one another are H, fluorine, OH, $(C_1-C_6)$-alkyl, $(C_5-C_6)$-cycloalkyl, $(C_5-C_6)$-cycloalkyl-$(C_1-C_6)$-alkanediyl, or R$^8$OR$^9$, R$^8$—$(C_5-C_{10})$-arylene-R$^9$, R$^8$R$^8$NR$^9$, R$^8$NHC(O)OR$^9$, R$^8$S(O)$_n$NHR$^9$, R$^8$OC(O)NHR$^9$, or R$^8$C(O)NHR$^9$;

$R^8$ is H, $(C_1-C_6)$-alkyl, $(C_5-C_6)$-cycloalkyl, $(C_5-C_6)$-cycloalkyl-$(C_1-C_2)$ alkanediyl, $(C_5-C_6)$-aryl, or $(C_5-C_6)$-aryl-$(C_1-C_2)$-alkanediyl;

$R^9$ is a direct bond or $(C_1-C_6)$-alkanediyl;

$R^{10}$ is C(O)R$^{11}$;

$R^{11}$ is OH, $(C_1-C_6)$-alkoxy, phenoxy, benzyloxy, $(C_1-C_4)$-alkylcarbonyloxy-$(C_1-C_4)$-alkanediyloxy, NH$_2$, or mono- or di-$(C_1-C_6$-alkyl)-amino;

n is 1 or 2;

p, q independently of one another are 0 or 1;

in all their stereoisomeric forms or mixtures thereof in any ratio; or their physiologically tolerable salts.

5. A compound of the formula (I) as claimed in claim 1, wherein A is $(C_1-C_8)$-alkanediyl-CO—NR$^2$—$(C_1-C_8)$-alkanediyl, —$(C_1-C_8)$-alkanediyl-CO—NR$^2$—$(C_1-C_8)$-alkanediyl.

6. A compound of the formula (I) as claimed in claim 1, which is 4-[2-(N-(imidazolin-2-yl)hydrazonoethyloxy)]benzoyl-(2S)-2-benzyloxycarbonylamino-β-alanine or its physiologically tolerable salts.

7. A process for the preparation of compound of the formula (I) as claimed in claim 1, in which $R^1$—Y—A is

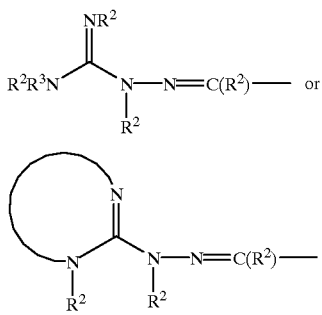

and B, D, E, F, G, $R^2$ and $R^3$ are defined as in claim 1, which comprises carrying out a condensation of a compound of the formula

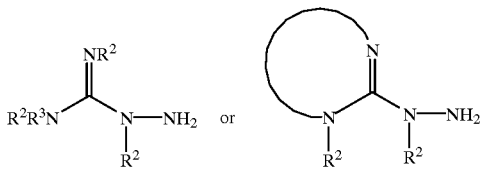

with a ketone or aldehyde of the type O═C(R²)—, in which R² and R³ are as defined above, or the corresponding acetal or ketal.

8. A process for the preparation of a compound of the formula (I) as claimed in claim 1, in which F is —C(O)NR²— and R¹, Y, A, B, D, E and G are defined as in claim 1, which comprises carrying out a condensation of a compound of formula (II)

R¹—Y—A—B—D—E—M           (II)

with HR²N—G, where R¹, R², Y, A, B, D, E and G are defined as above and M is hydroxycarbonyl or the acid chloride, active ester or mixed anhydride derivatives thereof or ($C_1$–$C_6$)-alkoxycarbonyl.

9. A pharmaceutical preparation comprising at least one compound of the formula (I) as claimed in claim 1 or a physiologically tolerable salt thereof as inhibitors of bone resorption by osteoclasts, as inhibitors of tumor growth and tumor metastasis, as antiinflammatories, for the treatment or prophylaxis of cardiovascular disorders, for the treatment or prophylaxis of nephropathies and retinopathies or as vitronectin receptor antagonists for the treatment and prophylaxis of diseases which are based on the interaction between vitronectin receptors and their ligands in cell—cell or cell-matrix interaction processes and at least one pharmaceutically innocuous excipient or additive.

10. A pharmaceutical preparation comprising at least one compound of formula (I) as claimed in claim 1 or its physiologically tolerable salts, and at least one pharmaceutically innocuous excipient or additive.

11. A method for inhibiting bone resorption by osteoclasts, inhibiting tumor growth and tumor metastasis, reducing inflammation, treating or preventing cardiovascular disorders, for treating or preventing nephropathies and retinopathies or for the treatment and prevention of diseases which are based on the interaction between vitronectin receptors and their ligands in cell—cell or cell-matrix interaction processes, comprising administering a therapeutically effective amount of a compound of formula (I) as claimed in claim 1 or a physiologically tolerable salt thereof to a human or animal in need thereof.

12. A method for inhibiting bone resorption by osteoclasts, comprising administering a therapeutically effective amount of a compound of formula (I) as claimed in claim 1 or a physiologically tolerable salt thereof to a human or animal in need thereof.

13. A method for inhibiting tumor growth and tumor metastasis, comprising administering a therapeutically effective amount of a compound of formula (I) as claimed in claim 1 or a physiologically tolerable salt thereof to a human or animal in need thereof.

14. A method for treating or prophylaxis of cardiovascular disorders, comprising administering a therapeutically effective amount of a compound of formula (I) as claimed in claim 1 or a physiologically tolerable salt thereof to a human or animal in need thereof.

15. A method for treating or prophylaxis of cardiovascular disorders, comprising administering a therapeutically effective amount of a compound of formula (1) as claimed in claim 1 or a physiologically tolerable salt thereof to a human or animal in need thereof.

16. A method for treating or prophylaxis of nephropathies and retinopathies, comprising administering a therapeutically effective amount of a compound of formula (I) as claimed in claim 1 or a physiologically tolerable salt thereof to a human or animal in need thereof.

17. A method for the treatment and prophylaxis of diseases which are based on the interaction between vitronectin receptors and their ligands in cell—cell or cell-matrix interaction processes, comprising administering a therapeutically effective amount of a compound of formula (I) as claimed in claim 1 or a physiologically tolerable salt thereof to a human or animal in need thereof, wherein the compound acts as vitronectin receptor antagonists.

\* \* \* \* \*

UNITED STATES PATENT AND TRADEMARK OFFICE
CERTIFICATE OF CORRECTION

PATENT NO.  : 6,005,117
DATED       : December 21, 1999
INVENTOR(S) : Volkmar Wehner, et. al.

It is certified that error appears in the above-identified patent and that said Letters Patent is hereby corrected as shown below:

Column 38, cancel claims 14 and 15 and add new renumbered claims 14 & 18.

-- 14. A method for reducing inflammation, comprising administering a therapeutically effective amount of a compound of formula (I) as claimed in claim 1 or a physiologically tolerable salt thereof to a human or animal in need thereof.

-- 18. A method for treating or prophylaxis of cardiovascular disorders, comprising administering a therapeutically effective amount of a compound of formula (I) as, claimed in claim 1 or a physiologically tolerable salt thereof to a human or animal in need thereof.--

Signed and Sealed this

Twenty-fifth Day of July, 2000

Attest:

Q. TODD DICKINSON

*Attesting Officer*     *Director of Patents and Trademarks*